United States Patent
Stewart et al.

(10) Patent No.: US 6,692,734 B2
(45) Date of Patent: Feb. 17, 2004

(54) N,O-AMIDOMALONATE PLATINUM COMPLEXES

(75) Inventors: Donald R. Stewart, Irving, TX (US); John R. Rice, Irving, TX (US); John V. St. John, Roanoke, TX (US)

(73) Assignee: Access Pharmaceuticals, Inc., Dallas, TX (US)

( * ) Notice: Subject to any disclaimer, the term of this patent is extended or adjusted under 35 U.S.C. 154(b) by 0 days.

(21) Appl. No.: 09/755,220

(22) Filed: Jan. 4, 2001

(65) Prior Publication Data

US 2001/0038830 A1 Nov. 8, 2001

Related U.S. Application Data

(60) Provisional application No. 60/174,435, filed on Jan. 4, 2000.

(51) Int. Cl.[7] ............................................. A61K 31/74
(52) U.S. Cl. ................ 424/78.27; 424/78.08; 424/78.16; 424/78.17; 424/78.18; 424/78.22; 424/78.23
(58) Field of Search .................... 424/78.08, 78.17, 424/78.16, 78.18, 78.22, 78.27, 78.26

(56) References Cited

U.S. PATENT DOCUMENTS

| 4,946,954 A | 8/1990 | Talebian et al. ............ 536/121 |
| 5,965,118 A | * 10/1999 | Duncan et al. ........... 424/78.27 |

FOREIGN PATENT DOCUMENTS

| EP | 0 281 412 A | 9/1988 |
| EP | 0 284 197 A | 9/1988 |

OTHER PUBLICATIONS

Gibson, D., Rosenfeld, A, Apfelbaum, H and Blum, J. 1990. Multinuclear NMR Studies of the Reactions between cis–Diaminequaplatinum(II) Complexes and Aminomalonate. Inorg. Chem. 29, 5125–5129.*
Patent Abstract of Japan vol. 014, No. 232 (C–07198) May 17, 1990.
Patent Abstract, JP 02 056421 A (Tanabe Seiyaku Co LTD), Feb. 26, 1990.
Patent Abstract of Japan vol. 014, No. 246 (c–0722) May 25, 1990.
Patent Abstract JP 02 067217 A (Tanabe Seiyaku Co LTD), Mar. 7, 1990.
Ohya, et al, "Antitumor drug delivery by dextran derivatives immobilizing platinum complex (II) through coordinating bond", 1998, 266–278, Acs Stmp. Ser.
Gandolfi, et al, "Sysnthesis of cis–dichlorodiammineplatinum analogs having steroidal hormones bound to the metal atom via malonato bridges", 1989, 113–123, Inorg. Chim. Acta.

* cited by examiner

Primary Examiner—Thurman K. Page
Assistant Examiner—Liliana Di Nola-Baron
(74) Attorney, Agent, or Firm—Bernard F. Rose, Esq.; Bingham McCutchen LLP

(57) ABSTRACT

The present invention relates to purified platinum complexes in which platinum is coordinated to form a single N,O- or O,O-chelate of an amidomalonate. The chelates, and pharmaceutically acceptable formulations thereof, are useful for the treatment of cancer. The platinum chelates may additionally be linked to one or more functional groups which increases water solubility and/or assists in tumor targeting of the chelate. Examples of tumor targeting moieties include polymers, in which one or more platinum chelates are attached to the polymer backbone via linkers capable of being cleaved in the body, and molecules with a high affinity for receptors which are concentrated or upregulated in tumor tissue and/or the tumor vasculature.

7 Claims, 10 Drawing Sheets cisplatin carboplatin oxaliplatin

O,O-chelate of amidomalonate

N,O-chelate of amidomalonate

N,O-AMIDOMALONATE PLATINUM COMPLEXES

CROSS-REFERENCED TO RELATED APPLICATIONS

Priority is claimed from provisional application U.S. Ser. No. 60/174,435 filed on Jan. 4, 2000, and incorporated by reference herein.

BACKGROUND OF THE INVENTION

Following the discovery of the anti-tumor activity of cisplatin (Rosenburg et al, 1969) extensive research has been conducted into areas related to the use of platinum complexes for the treatment of cancer. The anti-tumor activity of platinum compounds is believed to result from the loss of the labile chlorine ligand(s) in vivo to form a reactive mono- or di-aqua complex, which is able to form intra- and interstrand DNA crosslinks in tumor cells. These crosslinks can result in cell death. Cisplatin (cDDP or cis-diamminedichloroplatinum(II) is the most widely used of the platinum compounds approved for use in human subjects, and is indicated for the treatment of solid tumors, including testicular, ovarian, and head and neck, and in combination with other agents in use against squamous cell carcinoma and small cell lung carcinoma (Sur, et al., 1983).

However, there are significant limitations to the use of cisplatin due to its toxicity. Nephrotoxicity and ototoxicity are typically its dose limiting toxicities. Because of this problem, many researchers have made and tested novel small molecule platinum chelates in the hope of finding new compounds in which the therapeutic index (the ratio between the maximum dose that can be tolerated due to toxicity and the dose which provides efficacy) is improved. Changes in platinum chelate structure might also extend the spectrum of tumor types for which platinum therapy could be effective, and/or alter the toxicity profile. As noted above, labile leaving groups are required for tumorcidal activity, but these functional groups can also contribute to the toxicity of the molecule. Research conducted at the Institute for Cancer Research in the U.K. demonstrated that by replacing the chlorine atoms with other leaving groups, compounds could be obtained with lower nephrotoxicity (Harrap, 1985). This work led to the discovery of carboplatin, a cisplatin analog in which the two coordinated chloride ions are replaced by a chelate of 1,1-cyclobutane-dicarboxylic acid. This chelating group is less labile compared with the chlorine atoms of cisplatin. As a result, compared to cisplatin, higher doses of carboplatin are required for a similar tumorcidal effect, but carboplatin has a higher therapeutic index, and the dose limiting toxicity is myelosuppression rather than nephrotoxicity.

Oxaliplatin is another small platinum chelate approved for human use in Europe. This platinum chelate was the result of research investigating the effect of changes in both the non-labile (amine) ligand of cisplatin as well as the labile ligands. In oxaliplatin, the coordinated ammonia ligands are replaced by a trans-1R,2R-diaminocyclohexane (DACH) chelate, while the labile chlorine ligands are replaced by an oxalic acid chelate. It has been shown that oxaliplatin (and other DACH platinum compounds) have a different activity spectrum when compared with cisplatin and carboplatin in the NCI human tumor screen (Paull et al. 1989), and oxaliplatin was subsequently developed for the treatment of colorectal cancer. The dose limiting toxicity of oxaliplatin is sensory neuropathy.

Many other small platinum complexes have been investigated as potential chemotherapeutic agents, but at best, only slight improvements to efficacy and therapeutic index have been achieved. Many of these newer small platinum chelates are inactive or have formulation problems (for example, low solubility in water or poor aqueous stability), and most induce severe toxic side effects including nephrotoxicity, neurotoxicity, myelosuppression, nausea and vomiting. A number of attempts to improve the therapeutic index of the approved platinum complexes have involved either combination therapy, for example, the co-administration of cisplatin and paclitaxel; (Posner et al, 2000) or formulation changes, such as entrapment in liposomes (Steerenberg et al, 1988). There remains a distinct need for new platinum chelates with further improvements in therapeutic index compared with the currently-approved platinum chelates. Such chelates would ideally be water soluble and stable in an aqueous environment, but sufficiently labile in tumor cells to provide species capable of crosslinking DNA and ultimately causing tumor cell death.

Furthermore, improvements to therapeutic index might be achieved by targeting of platinum complexes to tumor cells. Conventional small molecule platinum complexes such as cisplatin, carboplatin, and oxaliplatin are not specifically targeted to tumor cells, and following intravenous administration, they can diffuse into normal cells as readily as they diffuse into tumor cells. Also, their doses are rapidly cleared. At 3 hour post injection 90% of plasma platinum from cisplatin is irreversibly protein bound (Physcan's. Desk Ref. 1997). For cisplatin and carboplatin 25% and 65%, respectively, of the dose is renally secreted within 12 h (DeVita et al. 1993). Improvements in therapeutic index might be possible if platinum complexes are more readily delivered to tumors and/or more readily taken up by tumor cells than normal cells.

One method of tumor targeting which has been extensively reported in the literature involves the labile attachment of a chemotherapeutic compound to a polymer or other macromolecular structure. It has been demonstrated that the concentration of polymers and nanoparticles in tumors exceeds their concentration in normal tissue following intravenous administration (Seymour 1992; Veronese et al. 1999). The mechanism for this preferred tumor accumulation has been termed the "enhanced permeability and retention" (or "EPR") effect (Seymour et al. 1995). Essentially, tumor endothelial cells are more 'leaky' than normal endothelial cells, so polymers and nanoparticles more readily cross the endothelial cell layer in tumors than is the case in normal tissue. Thus, following intravenous administration, polymers and nanoparticles can enter the extracellular fluid of tumor cells much more readily than that of normal cells. Furthermore, lymphatic drainage of the extracellular fluid in tumor cells is much less efficient compared with normal cells. These two factors account for the greater concentration of polymers and nanoparticles in tumors relative to normal tissue relative to small, freely diffusible molecules.

There are already several examples of constructs which provide for the passive targeting of chemotherapeutic agents to tumors through the EPR effect. For example, doxorubicin was attached to a polyhydroxypropylmethacrylamide, (poly (HPMA)), linear polymer backbone via a tetrapeptide designed to be cleaved by lysosomal enzymes. The water-soluble conjugate was termed 'PK1', and has been subject of numerous publications describing its chemistry, pre-clinical testing, and clinical evaluation (for example, Seymour et al, 1990; Pimm et al, 1996; Duncan et al. 1998; Thomson et al. 1999; Minko et al. 2000). Similarly, HPMA was conjugated to paclitaxel and camptothecin for enhanced delivery of these chemotherapeutic molecules to tumors (Fraier et al, 1998; Caiolfa et al. 2000). Both paclitaxel and camptothecin have been attached to other water-soluble polymers for the purpose of improving tumor targeting and drug water solubility (for example, Li et al. 2000 and Conover et al. 1998).

It has been proposed that polymer-platinum conjugates might be used to benefit patients in treating cancer by increasing the solubility of platinum complexes, reducing systemic toxicity, and targeting tumors by the EPR effect (Duncan 1992). Several examples of polymer-platinum conjugates have been reported. For example, U.S. Pat. No. 5,965,118 describes various platinum chelates attached to the HPMA polymer backbone via a peptide which is potentially cleavable by lysosomal enzymes (see also Gianasi et al. 1999). Additional examples include polyphosphazene platinum (II) conjugates (Sohn et al. 1997; U.S. Pat. No. 5,665,343), poly(glutamate) platinum complexes (Schechter et al. 1987), and others (Bogdanov, Jr., et al., 1996; Han, et al., 1994; Johnsson et al. 1996; Fiebig, et al., 1996); Filipova-Voprsalova et. al., 1991; Fuji et al. 1996; Neuse, et al., 1995; Schechter, et al., 1989).

To our knowledge, none of the above reports of polymer platinum conjugates provides good evidence of structure or nature of the platinum complexation to the polymer, although most make certain unsubstantiated assumptions about the structure of the platinum complex. In all these prior examples, it is possible for platinum to bind to the polymer in more that one way, thus giving rise to the possibility of mixed complexes. Also, pH is not controlled in the formation of the complexes which can lead to the formation of other platinum complexes which an be inactive (hydroxo ligands) or very toxic (aqua ligands). Thus, it is possible that platinum will be released from any one polymer at different release rates, and that the rate of platinum release will vary from batch to batch (as the mixture of complexes formed may vary between batches), giving rise to uncontrolled batch-to-batch variation in both toxicity and efficacy. Such variation is unacceptable for the use of these conjugates in the treatment of cancer. A preferred situation is to have well-defined and well-controlled complexation of platinum to the polymer, that gives a rate of release which is beneficial for the treatment of cancer when utilizing the EPR effect for the improved delivery of platinum compounds to tumors.

In addition to passive tumor targeting utilizing the EPR effect, it may also be possible to target platinum complexes to tumors utilizing 'active' mechanisms. This can be achieved, for example, by the coupling of a platinum complex to a moiety which binds to a receptor which is up-regulated in tumors compared with normal tissue, so giving rise to increased levels of platinum in tumor tissue compared to normal tissue. A wide variety of such up-regulated receptors are known (for example, Heppeler et al, 2000; Schlaeppi et al. 1999; Sudimack et al. 2000; Dubowchik et al. 1999; Weiner, 1999; Buolamwini, 1999). Examples of targeting agents include monoclonal antibodies, peptides, somatostatin analogs, folic acid derivatives, lectins, and polyanionic polysaccharides.

However, to our knowledge there are very few reported examples of the utilization of receptor-targeting mechanisms for the increased delivery of platinum to tumor tissue. Studies of platinum conjugated with monoclonal antibodies (McIntosh et al, 1997; Hata et al, 1992), with steroids (Gust et al, 1995; DiZio et al, 1992, Gibson, et al. 1990) and with folic acid (Vitols et al, 1987), but none have been evaluated in the clinic.

It is also possible to combine the passive targeting of a polymer with the active targeting of a receptor-avid compound. This is exemplified by "PK2", a compound which has a HPMA polymer, doxorubicin attached to the polymer via an enzyme-cleaveable peptide, and is conjugated with galactose, a carbohydrate with strong affinity for the asialoglycoprotein receptor, which is highly concentrated in the liver (Julyan et al, 1999). To our knowledge, this approach, of combining active and passive targeting, has not been explored with platinum chelates.

The present invention is based upon the unexpected discovery of conditions that allow the initial unstable O,O-amidomalonate cis-diamineplatinum(II) complex to rearrange to a pure and isolable N,O-amidomalonate cis-diamine platinum(II) complex. An O,O—Pt chelate is initially formed when reactive cis-diamineplatinum(II) species react with amidomalonates. Reports discussed below indicate that in such reactions either no N,O-chelate is formed or is found as minor products which were not isolated or purified. Here, general conditions are described which allow a pure N,O-amidomalonate-diamineplatinum (II) to be isolated. Further, such N,O-chelates have preferential biological activity for the treatment of cancer, specifically an improved therapeutic index. The beneficial properties of such N,O-amidomalonate chelates for the treatment of cancer have not previously been reported. Furthermore, the near complete conversion of less thermodynamically-stable complexes to the N,O-chelates described herein provides small molecule and polymeric compounds for treating tumors which can be manufactured with a consistent efficacy and toxicological profile.

For any pharmaceutical product, accurate measures of its identity and purity are necessary. For the present invention and related areas it is most important to verify the exact nature of the platinum complex and identify impurities, for there are examples where an impure platinum complex showed promising biological activity which disappeared upon purification (Talebian et al. 1991 and Appleton et al. 2000).

For the present invention the best method to identify the exact nature of the platinum complex is NMR spectroscopy, specifically $^{195}$Pt NMR and $^{15}$N NMR spectroscopies (Appleton 2000). With either technique, determination of the identity of platinum complexes is made without the need for prior separation. For this work $^{195}$Pt NMR spectroscopy is the method of choice, for it provides sufficient sensitivity and avoids the need for isotopic enrichment required for $^{15}$N NMR spectroscopy. $^{195}$Pt nuclei are spin ½, possess a receptivity nearly twenty times that of $^{13}$C nuclei, and show resonances across a chemical shift range of 15,000 ppm. The chemical shift is very sensitive to the identity and geometry of the platinum ligands. $^{195}$Pt has a practical sensitivity limit of about $\geq$10 mM platinum. Examples of the chemical shifts for cis-diammine platinum(II) complexes include: −2168 ppm for cisplatin, −1723 for carboplatin, −1584 ppm for diaqua, −1841 ppm for monoaqua-monochloro, −1732 ppm for O,O-aminomalonate, −2156 ppm for N,O-aminomalonate, and −2020 ppm for N,O-chelate of N-acetylglycine (Appleton 1990; Gibson 1990; Appleton 2000). Corresponding DACH-Pt complexes appear further upfield.

Reactions of cis-diamineplatinum(II) species with the free amine containing aminomalonate have been documented. Gandolfi (Gandolfi, et al. U.S. Pat. No. 4,614,811; Gandolfi, et al. 1987) reported the preparation and antitumor activity of complexes between cis-diamine platinum(II) species and aminomalonate. The reported structures were all O,O-chelates as shown in FIG. 2a. Later, it was clearly shown (Appleton et al. 1990 and Gibson et al. 1990) that although the O,O—Pt chelate is formed first, it isomerizes to the thermodynamic N,O-aminomalonate cis-diamineplatinum (II) complex shown in FIG. 2b within a few hours at a pH=5. Furthermore, Appleton showed that if the pH was too low (<2) decarboxylation occurred to give the corresponding N,O-glycine complex. If the pH was too high (>9) hydrolysis of the platinum ester occurred. Literature reports of the biological activity of pure N,O-aminomalonate complex are not known. However, a report (Talebian 1991) of a closely related well purified N,O-aspartate cis-diamine Pt(II) complex showed little if any cytotoxic activity. For cis-diamineplatinum(II) complexes of amidomalonates like those shown in FIG. 3 (no free amine) Tsujihara in U.S. Pat. No. 4,882,447 reports the preparation and biological activity of a number of O,O-amidomalonate complexes of 1,2-diaminecyclohexaneplatinum(II) (i.e. DACH-platinum(II)). Data verifying the O,O—Pt chelation was not described. A series of amidomalonate DACH-platinum(II) were reported to only exist as O,O—Pt chelates like that shown in FIG. 3a (Talebian et al. 1990). A polyphosphazene based amidomalonate was shown as only an O,O-chelate (FIG. 3a), with no confirming spectroscopic data though a similar glutamate based material showed about equal amounts of the two chelates. However, a series of steroid based amidomalonate-diamineplatinum(II) complexes (FIG. 3, R=steroid) were shown to be a mixture of O,O—Pt and N,O—Pt amidomalonate chelates (FIGS. 3a and 3b, respectively), with the O,O-isomer being predominant (Gibson et al. 1990). No separation of the two species was described although it was speculated that perhaps with heat or longer reaction times the N,O-chelate could be favored. However, this invention shows that additional components are required to effect the O,O—Pt to N,O—Pt conversion of amidomalonate cis-diamine platinum complexes.

In summary, for cis-diamine platinum(II) complexes of aminomalonate the initial O,O—Pt chelate rapidly isomerizes to the N,O—Pt chelate. However, for cis-diamine complexes of amidomalonates, either the O,O—Pt chelate is only found or the O,O—Pt chelate predominates in mixtures of both chelates. No reports have been found on the preparation of pure N,O-chelate of amidomalonates. Accordingly, the preparation and useful biological activity of the N,O-chelate of cis-diamineplatinum(II) complexes with amidomalonate is now presented. Additionally, the selective preparation of the O,O-chelate is described.

SUMMARY OF THE INVENTION

The present invention involves a purified N,O-amidomalonate platinum diamine complex. This complex may be polymer bound. This complex is useful in a method of treating a platinum sensitive neoplasia that involves administering an effective amount of a purified N,O-amidomalonate diamine complex to a patient.

In greater detail, the present invention involves a composition for use in tumor treatment, comprising a cis-diamine N,O-amidomalonate platinum species of the form:

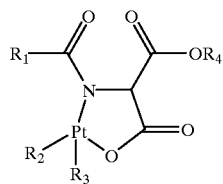

where $R_1$ is H, alkyl, a water solubilizing group, carrier or a targeting group useful for targeting the species to a tumor;

$R_2$ and $R_3$ are amines; $R_4$ is H or a cation; and where said species has, or is converted in vivo to have, anti-tumor activity. The cation in this complex may be an ammonium ion, an alkali, or an alkali earth metal. A preferred cation is sodium.

In certain cases, the N,O-amidomalonate platinum diamine complex may involve the above composition, wherein $R_1$ is a synthetic polymer of N-alkyl methacrylamide units of molecular weight from 1–5000 kDaltons and the form:

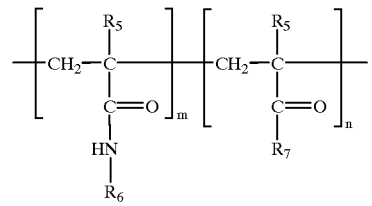

where m=0 and n=100 or where the ratio of m:n is 0.1–99.9; where $R_5$ is H or $CH_3$; where $R_6$ is a $C_1$–$C_6$ hydroxyalkyl group and where $R_7$ is an oligopeptide chain capable of being cleaved under physiological conditions with the sequence of Gly-(W)$_P$-Gly where p is 0–3 and W is an amino acid or combination of any amino acids and whose C terminus is an amide of the amido malonato group.

In an important embodiment of the above N,O-amidomalonate platinum complex both $R_2$ and $R_3$ are in $NH_3$. These are often preferably, the primary amine groups of 1,2-diaminocyclohexane.

The platinum involved in these complexes may be in the +2 or +4 oxidation state. $R_1$ as mentioned above is either H or alkyl, but may also be a steroid or a folic acid or a folic acid derivative or analog useful to target folate receptors.

The polymer of the polymer N,O-amidomalonate platinum complex may be, along with other polymers described herein, a polyglutamic acid, a mono- or polysaccharide or the side chain of a polysaccharide.

The present invention also involves a method of improving the stability of a platinum diamine compounds. This method involves forming a purified N,O-amidomalonate complex of the platinum compound.

In an important aspect of the present invention involves a composition for use in tumor treatment, comprising a polymer-platinum complex designed to accumulate at a tumor site and composed of an N-alkyl acrylamide polymer having side chains spaced along the polymer for complexing with a platinum compound, said side chains (i) composed of an oligopeptide attached at one end to the polymer and at the other end, at least primarily via a N,O-amidomalonate complex, to the platinum compound and (ii) including at least one linkage designed to be cleaved under selected physiological conditions to yield a platinum compound which has, or is converted in vivo to have, anti-tumor activity.

Such an N-alkyl acrylamide polymer is preferably a homopolymer having a molecular weight of between about 1,000 and about 5,000,000 Daltons. The N-alkyl acrylamide polymer may be a copolymer having two repeat units m and n in a ratio m:n of between 0.1 and about 99.9.

The compositions of the present invention may also involve repeat units of an N-alkyl acrylamide unit carrying oligopeptide side chains. These oligopeptide side chains may terminate in a proximal group capable of attaching the platinum compound.

In the compositions of the present invention, the useable polymer may be a copolymer of the form where the polymer is a copolymer of the form:

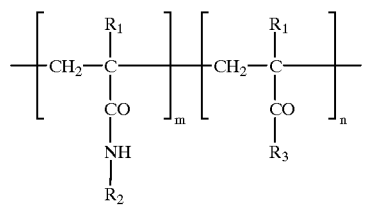

where $R_1$ is H or $CH_3$, $R_2$ is a lower alkyl or lower hydroxyalkyl group, and $R_3$ is an oligopeptide side chain. In this polymer, $R_1$ is $CH_3$, $R_2$, is 2-hydroxypropyl, and $R_3$ is Gly-Phe-Leu-Gly-Ama or Gly-Gly-Ama. In therapeutic uses of the present invention, the polymer platinum compound is dissolved in a aqueous medium suitable for parenteral administration.

An important aspect of the present invention is a method of treating a solid tumor in a subject with a platinum compound, the method comprising preparing a polymer-platinum complex composed of an N-alkyl acrylamide polymer having side chains spaced along the polymer for complexing with a platinum compound, said side chains (i) composed of an oligopeptide attached at one end to the polymer and at the other end to the platinum compound via a N,O-amidomalonate complex and (ii) including at least one linkage designed to be cleaved under selected physiological conditions to yield the platinum compound which has, or is converted in vivo to have, anti-tumor activity; and parenterally administering a pharmaceutically effective amount of the complex to the subject. Said N-alkyl acrylamide polymer in one preferable embodiment is a homopolymer having a molecular weight of between about 1,000 and about 5,000,000 Daltons. In another important embodiment the N-alkyl acrylamide polymer is a copolymer having a molecular weight between 1,000 and 5,000,000 Daltons. This copolymer contains two repeat units m and n in a ratio of m:n between 0.1 and about 99.9. Such repeat units comprise an N-alkyl acrylamide unit and a unit carrying an oligopeptide side chain having a proximal end capable of attaching to a platinum compound. When an oligopeptide is used, said oligopeptide is preferably Gly-(W)$_p$-Gly where p is 0–3 and W is an amino acid or combination of any amino acids. In one important embodiment the oligopeptide is Gly-Phe-Leu or Gly-Gly.

This invention comprises a method enhancing the therapeutic index of a platinum diamine compound when the compound is used for treating a tumor by parenterally administering a pharmaceutically acceptable solution containing the compound to a subject, comprising prior to said administering, complexing the platinum compound with a copolymer composed of an N-alkyl acrylamide first repeat unit and a second repeat unit having an oligopeptide side chain having an amidomalonate end group complexing via N,O linkages with said platinum compound.

From another view, this invention involves a method of improving the stability of a platinum diamine compound comprising complexing the compound with a copolymer composed of an N-alkyl acrylamide first repeat unit and a second repeat unit having an oligopeptide side chain having an amidomalonate end group complexing with said platinum compound through an O,N-linkage.

Accordingly, it is an object of the invention to provide new polymer-platinum complexes having improved antitumor activity in vivo.

In one aspect, the invention includes a composition for use in tumor treatment, comprising polymer-platinum compounds designed to accumulate at a tumor site. The compound is composed of a synthetic polymer backbone having platinum-containing side chains attached to the backbone. The side chains (i) are composed of a biodegradable linker, for example, an oligopeptide attached at or near one end to the backbone and at or near the other end to a platinum compound. The linker includes at least one linkage which is designed to be cleaved under selected physiological conditions to yield the platinum compound which has, or is converted in vivo to have, anti-tumor activity. The oligopeptide may contain more than the usual amino acids, e.g., aminomalonate and the like or other than alpha amino acids.

In one embodiment, the synthetic polymer is a homopolymer of an N-alkyl acrylamide or methacrylamide (i.e. all 'n' type repeat units) having a molecular weight of between about 1,000–5,000,000 Daltons.

In another embodiment, the synthetic polymer is a copolymer having a molecular weight between 1,000 and 5,000,000 Daltons and contains two repeat units m and n in a ratio m:n of between about 0.1 and 99.9.

The repeat units, in one embodiment, are composed of an N-alkyl acrylamide or methacrylamide unit and of a unit carrying the oligopeptide side chain which terminates in a proximal end group capable of attaching the platinum compound.

In one embodiment, the polymer in the polymer-platinum compound is a copolymer of the form:

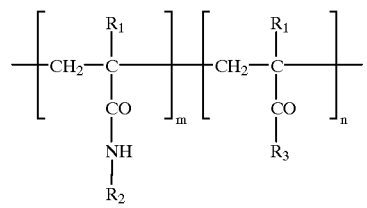

where m=0 and n=100 or where the ratio of m:n is 0.1–99.9; where $R_1$ is H or $CH_3$, $R_2$ is a lower alkyl or lower hydroxyalkyl group, and $R_3$ is a oligopeptide side chain.

The oligopeptide is, in another embodiment, an oligopeptide of the form Gly-(W)$_p$-Gly where p can be 0 to 3 and (W) can be any amino acid or combination of any amino acid. In one embodiment, the peptide is Gly-Phe-Leu-Gly and terminates in a carboxyl, diamine or malonyl moiety for attachment to the platinum compound. The Phe or Leu are (L) amino acids in the preferred embodiment. In another embodiment, the peptide is Gly-Gly terminating in a proximal carboxyl end group. To the extent that D-amino acid-containing oligopeptides are biodegradable, they too may be part or all of an oligopeptide.

In a preferred embodiment, $R_1$ is $CH_3$, $R_2$ is 2-hydroxypropyl, and $R_3$ is Gly-Phe-Leu-Gly-[X] where [X] is a diamine, a carboxyl group or a malonyl moiety.

The polymer-platinum compound is dissolved in a pharmaceutically acceptable medium suitable for parenteral administration.

In another aspect, the invention includes a method of targeting a platinum compound to a solid tumor in a subject. The method includes preparing a polymer-platinum compound composed of a synthetic polymer backbone having side chains spaced along the backbone. The side chains (i) are composed of an oligopeptide attached at one end to the backbone and at the other end to a platinum compound and (ii) include at least one linkage which is designed to be cleaved under selected physiological conditions to yield the platinum compound which has, or is converted in vivo to have, anti-tumor activity. The compound is parenterally administered in a pharmaceutically effective amount to the subject.

In another aspect, the invention includes a method of enhancing the therapeutic index of a platinum compound, when the compound is used for treating a tumor by administering parenterally a pharmaceutically acceptable solution containing the compound to a subject. The method includes, prior to administering the compound, complexing the platinum compound with a copolymer composed of an N-alkyl acrylamide first repeat unit and a second repeat unit having an oligopeptide side chain which terminates in a proximal end group capable of complexing with the platinum compound.

In another aspect, the invention includes a method of improving the solubility and/or stability of a platinum compound by complexing the compound with a copolymer composed of an N-alkyl acrylamide first repeat unit and a second repeat unit having an oligopeptide side chain which terminates in a proximal end group capable of complexing with said platinum compound. The polymer-platinum complex is more soluble and/or more stable under physiological conditions than non-complex platinum compounds. A preferred platinum complex is bound through—and O- of most preferably an amidomalonate residue connected to a biodegradable linkage to a polymer.

These and other objects and features of the invention will be more fully appreciated when the following detailed description of the invention is read in conjunction with the accompanying drawings.

Polymer-based delivery of therapeutic agents, including chemotherapeutic drugs, continues to receive considerable attention (Duncan et al (1999), Seymour). Typically, a well-established pharmacological entity is chemically linked to a biologically inert polymer, thus profoundly altering its distribution, elimination, and toxicological properties. For oncological applications, this technology offers the potential of increasing the concentration of the cytotoxic agent within the tumor interstitium via the enhanced permeability and retention (EPR) effect (Seymour, et al). ACCESS Pharmaceuticals has rights to a broad class of platinated polymer therapeutics. One of these, designated AP 5280, is a 90:10 copolymer of N-(2-hydroxypropyl)methacrylamide (HPMA) and the methacrylamide of Gly-Phe-Leu-Gly with an aminomalonato chelate of cis-diammineplatinum(II). Incorporation of this optimized linker offers the potential to release platinum-containing fragments from the polymer via cleavage by tumor proteases. The concept of this copolymer-linker-chelate combination, and early synthetic and biological studies, have been presented by Duncan et al (1999). The challenge in further developing this material for clinical evaluation has been to define a scalable procedure for a structurally-characterized product having the requisite activity, stability, and pharmaceutic properties necessary to secure regulatory approval for use in humans.

The synthesis of AP 5280 is accomplished by initially substituting diethyl aminomalonate for p-nitrophenol in the intermediate poly(HPMA) GFLG-ONp to give poly(HPMA)-GFLG-Ama-diEt. The latter is saponified, then platinated with cis-$(NH_3)_2Pt(H_2O)_2^{2+}$ to give poly(HPMA)-GFLG-Ama=Pt$(NH_3)_2$. This is followed by the controlled rearrangement of the initial O,O—Pt chelate to the N,O—Pt chelate. We have also made (Polymer Labs) the poly(HPMA)-GFLG-Ama-diEt from the HPMA and MA-GFLG-Ama-diEt monomers. By polymerizing these monomers with various amounts of a radical chain transfer agent (i.e. p-nitrophenol) the molecular weight is controlled. (Note: this method of control of molecular weight is well known in the literature.) These polymers were then saponified, platinated, and rearranged to give the N,O-chelate as described. Purification from low-molecular weight impurities is achieved by tangential-flow filtration, with isolation of the final formulated product by terminal lyophilization. The identity and purity of the N,O—Pt chelate (>92%) is confirmed by $^{195}$Pt NMR spectroscopy (−2056 ppm), with <8% Pt present as the O,O-chelate (−1733 ppm) or other Pt species. The final product contains 8.0±0.5% Pt (wt/wt) and has a $M_w$=24.4 kDa.

In water, AP 5280 releases <<1% of the platinum content as polymer-free platinum species, and releases <2% of the platinum into medium containing physiological concentration of chloride over 24 hours at 37° C. The efficacy of AP 5280 was evaluated in a s.c. B16F10 murine tumor model, which showed activity at 20 mg Pt/kg equivalent to that of cisplatin at 3 mg/kg. Activity superior to carboplatin (45 or 60 mg/kg) is achieved with AP 5280 at 200 mg Pt/kg (all doses IV, qd×5). In an important aspect, Figure A summarizes the process for the AP 5280 procedure.

Figure 5:
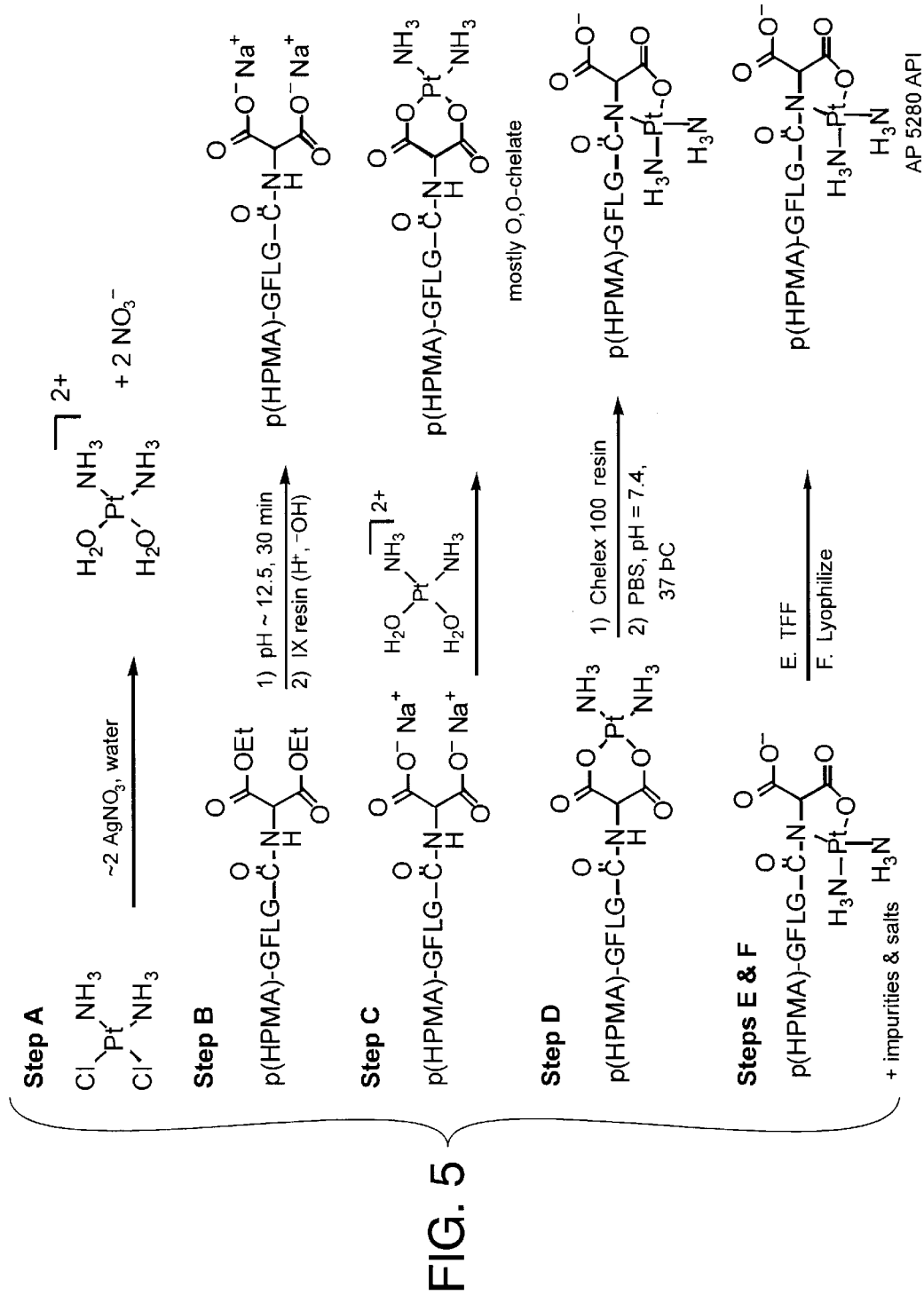
FIG. 5 shows the scheme used to prepare poly(HPMA)-GFLG-Ama=Pt$(NH_3)_2$N,O-Chelate. Many of these same steps and conditions given in examples are applicable to formation of other N,O-chelates of amidomalonate-cis-diammineplatinum(II) species be they a small molecule or attached to polymer.
Figure 8:
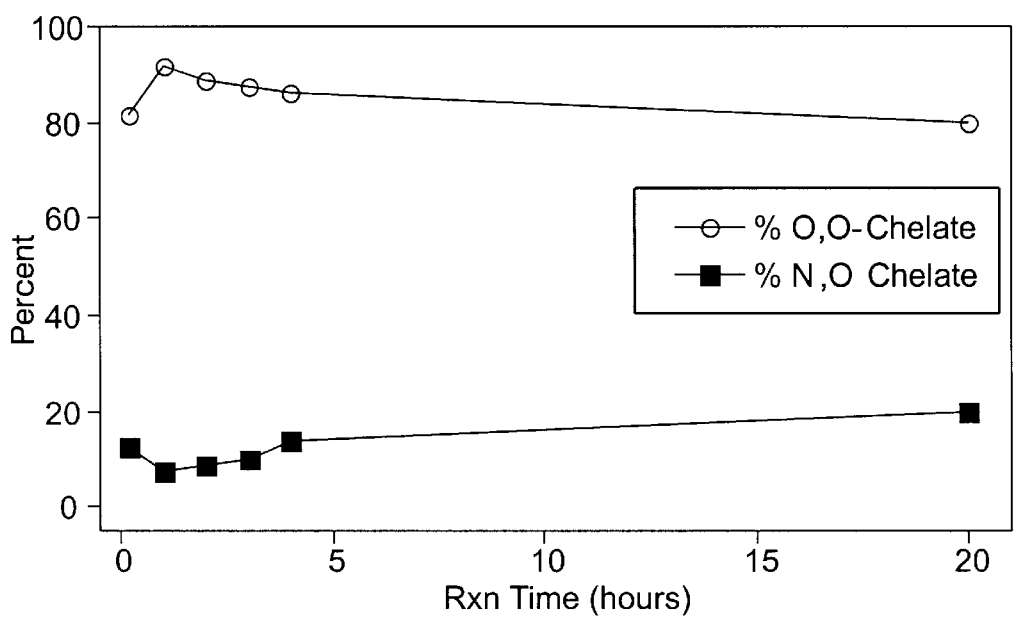

FIG. 8 shows a plot of the Percent O,O- and N,O Chelates during Step C of FIG. 5. This indicates that the O,O-chelate formation is complete within 1–2 hours.

Figure 9:
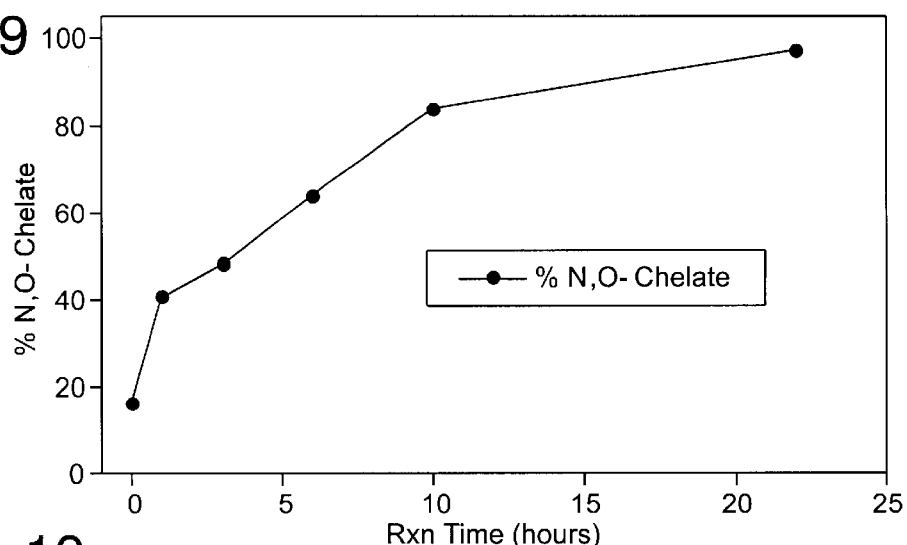

FIG. 9 shows a plot of the conversion of O,O- to N,O-chelate in 75 mM phosphate pH=7.4, 100 mM NaCl versus time. It indicates that with these conditions that 100% of the platinum exists as the N,O-chelate.

Figure 10:
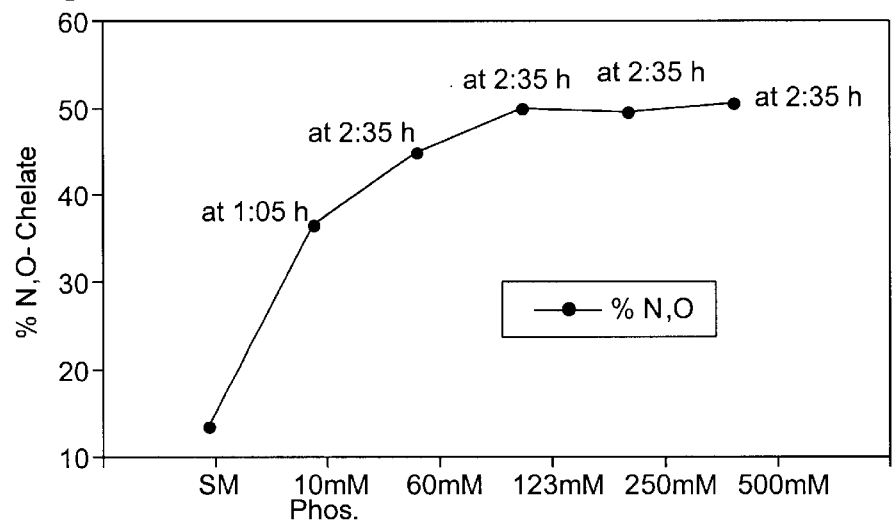

FIG. 10 shows the effect of chloride ion concentration on the O,O- to N,O-chelate conversion. The rate of chelate conversion at concentration above 60 mM NaCl are the same.

Figure 11:
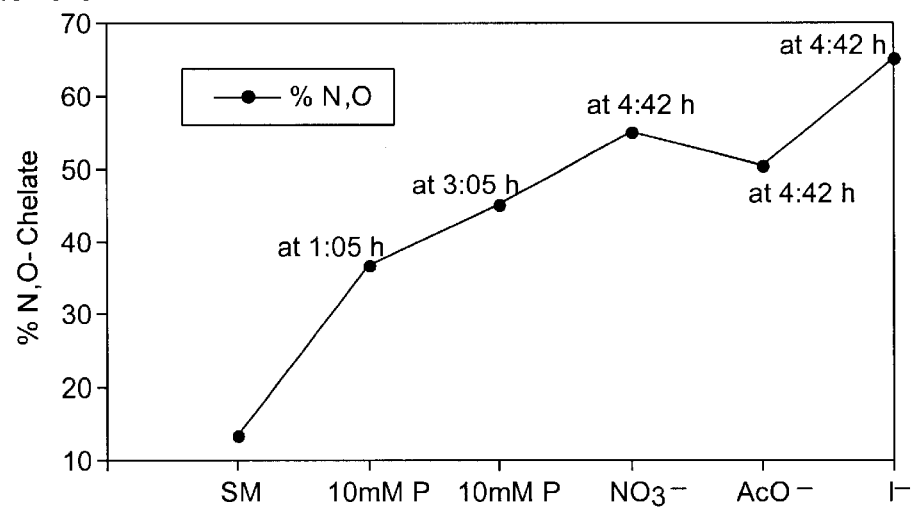

FIG. 11 shows the effect of nitrate, acetate, and iodide upon the O,O- to N,O-chelate conversion. All three anions effect the chelate conversion but at different rates.

Figure 12:
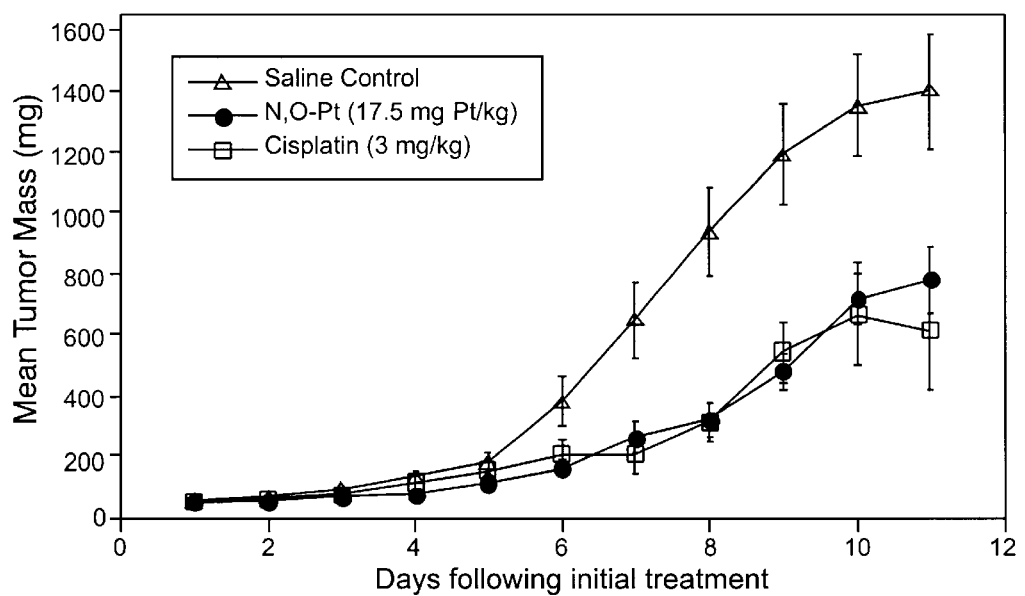

FIG. 12 shows a plot from the B16 melanoma tumor growth inhibition study of Example 23 where saline was used as a control, cisplatin was dosed near its MTD, and the N,O-chelate of poly(HPMA)-GFLG-Ama=Pt(NH$_3$)$_2$ was dosed well below its MTD.

Figure 13:
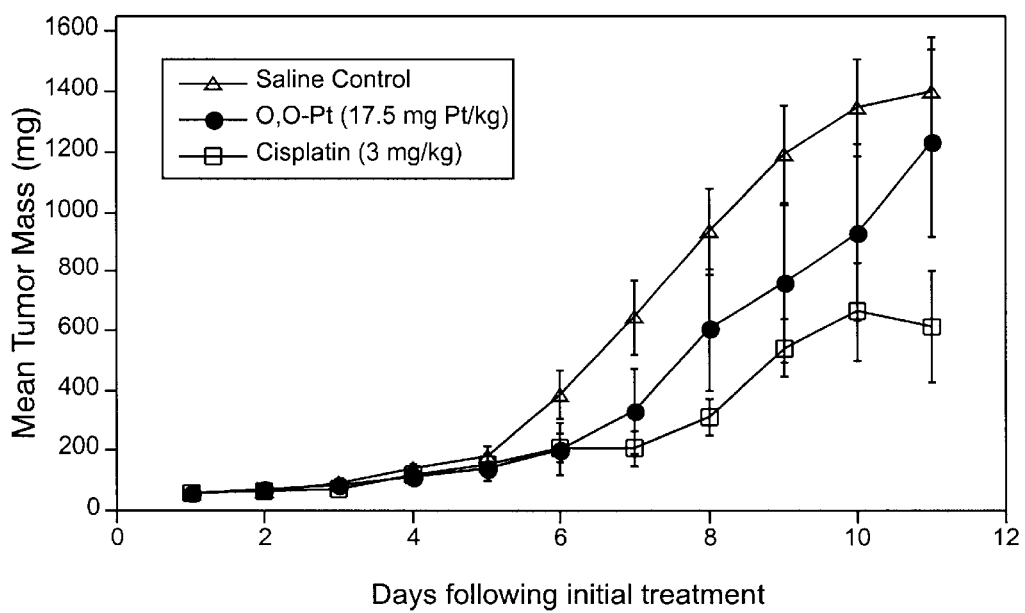

FIG. 13 shows a plot from the B16 melanoma tumor growth inhibition study of Example 24 where saline was used as a control, cisplatin was dosed near its MTD, and the O,O-chelate of poly(HPMA)-GFLG-Ama=Pt(NH$_3$)$_2$ was dosed near its MTD.

Figure 14:
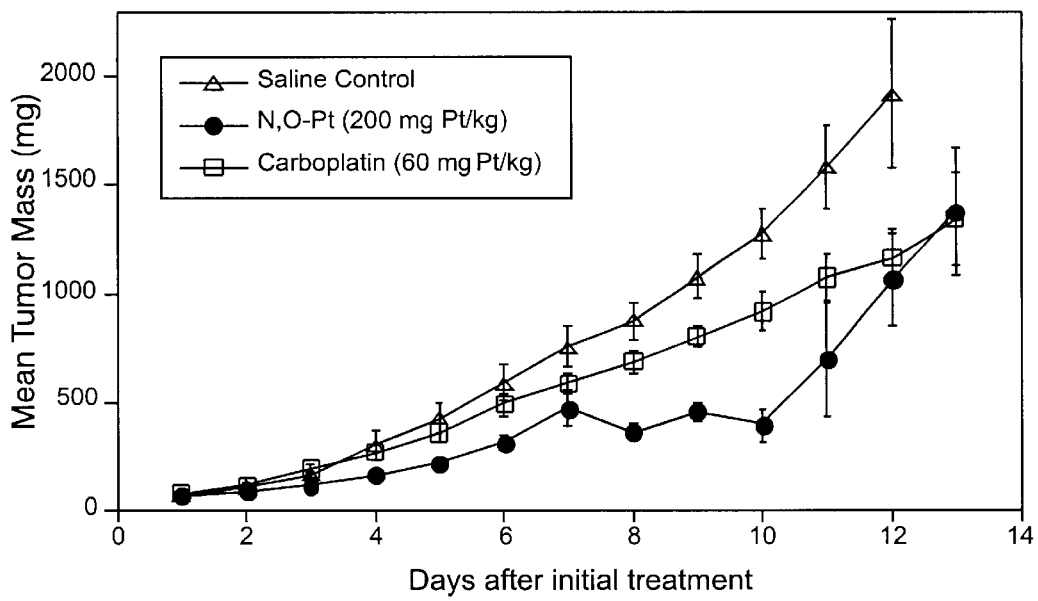

FIG. 14 shows a plot from the B16 melanoma tumor growth inhibition study of Example 25 where saline was used as a control, carboplatin was dosed near its MTD, and the N,O-chelate of poly(HPMA)-GFLG-Ama=Pt(NH$_3$)$_2$ was dosed near its MTD.

Figure 15:
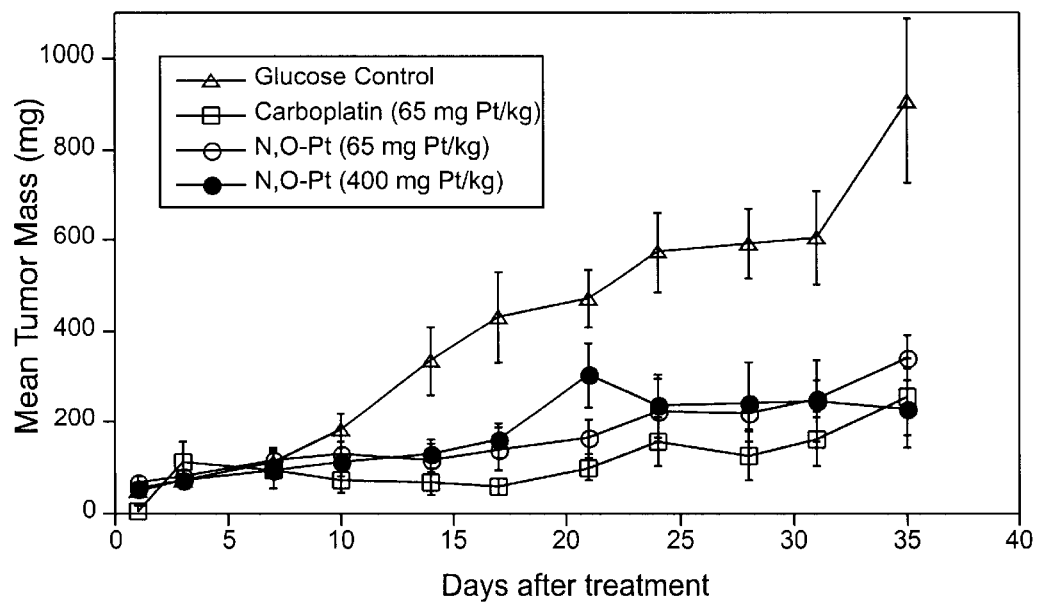

FIG. 15 shows a plot from the human xenograft tumor growth inhibition study of Example 26 where isotonic glucose was used as a control, carboplatin was dosed near its MTD, and the N,O-chelate of poly(HPMA)-GFLG-Ama=Pt(NH$_3$)$_2$ was dosed well below and near its MTD.

DETAILED DESCRIPTION OF THE INVENTION

A central embodiment of the invention is a purified and well characterized composition of a specific type of platinum(II) complex (i.e. FIG. 3b) in which an amidomalonate group is chelated to a platinum by the amide nitrogen of the amidomalonate and an oxygen of one of the carboxylates of the amidomalonate and where two other available ligand sites on the central platinum are ammines or amines. Such complexes may be useful chemotherapeutic agents in the treatment of cancer.

In an important aspect of the invention the R group (see FIG. 3b) connected to the carbonylamide of the N,O-amidomalonate-diamineplatinum(II) complex can be H, an alkyl group, a group useful to solubilize the inventive species, a polymer, a group useful to link between the inventive complex and a polymer, a macromolecule, or as a link to an entity useful to target the N,O-amidomalonate-diamineplatinum(II) complex to a tumor.

The present invention where the R group of the amide carbonyl is an H, a simple alkyl, or water solubilizing group may be useful, because the inventive N,O-amidomalonate-diamineplatinum(II) complexes have a favorable therapeutic index. Since the present examples show that the inventive N,O-chelates have low toxicity and good in vitro activity, such simple small molecule versions of N,O-amidomalonate-diamineplatinum(II) complexes may be useful. It is known that their O,O-chelate counterparts have biological activity, and the present invention shows that the O,O—Pt amidomalonate chelates rapidly convert to the N,O—Pt chelate under physiological conditions. By incorporating a water-solubilizing group as or part of the R group more favorable formulations and dosing may be attained. Such water solubilizing groups include but are not limited to carbohydrates, polyethyleneglycols, quaternized amines (i.e. betaine) and others known to those with skill in the art.

The present invention where the R group of the amide carbonyl is a polymer may be useful for the polymer can provide targeting to the tumor by the EPR effect as well as increase water solubility. The polymer can be synthetic or natural. Synthetic polymers include, but are not limited to, polyacrylamides including polymethacrylamides, polyacrylic acid, polymethacrylic acid, polyethyleneglycols (straight chained or branched) and polyaminoacids. Polyaminoacids include polyglutamate, polyaspartate, and polylysine. The polymer backbone in these polyaminoacids may be amides of the alpha amine and alpha carboxyl groups or carboxyl or amine groups of the side chains. Others may be apparent to those with skill in the art. Natural polymers include proteins such as albumin and polysaccharides such as heparin, chondroitin 6-sulfate, hyaluronate, dermatan sulfate, keratan sulfate, chitin, chitosan, etc. Others may be apparent to those with skill in the art. Each polymer strand may be bound to one or many platinum chelates. The connection between the polymer and the amidomalonate group can be made by substituting a polymer's carboxyl group with aminomalonate, using a dicarboxylic acid (for example succinic acid) to bridge between an amine group of a polymer and the amine of aminomalonic acid, or by forming an ether between a hydroxyl group of a polysaccharide and an amidomalonate with an alkyl halide substituent. Other possibilities may be apparent to those with skill in the art.

The present invention where the R group of the amide carbonyl contains a group useful to target the N,O-amidomalonate-diamineplatinum(II) complex to a tumor may be useful to further increase the therapeutic index of the inventive complex. Targeting agents include, but are not limited to, monoclonal antibodies, peptides, steroids, somatostatin analogs, folic acid derivatives and analogs, lectins, and polyanionic polysaccharides. Within this particular scope of the invention a covalent link between the inventive N,O-amidomalonatediamineplatinum(II) complex is made and the targeting group. Then, when such a targeted complex is administered to a patient the targeting agent will direct the inventive complex to the tumor. It is expect that this will increase the tumorcidal effect and decrease the systemic toxicity of the inventive platinum complex. One example of such a targeted complex could be made by substituting the gamma-carboxylate of folate with diethylaminomalonate to give a folate-Ama-diEt species. Then following the procedures given in the examples this would be converted to folate-Ama=Pt(NH$_3$)$_2$ N,O—Pt chelate. The platinum could be in either the +2 or +4 oxidation state.

In one preferred embodiment, the R group of the amide carbonyl group of amidomalonte is 'poly(HPMA)-GG-' the Ama group is attached to the proximal G (glycine). In a particularly preferred embodiment the amide carbonyl R group is 'poly(HPMA)-GFLG-' with M$_w$ of 25 kDa. Another preferred embodiment is where the amide carbonyl R group is 'poly(Glu-Ama)'.

Figure 3A:
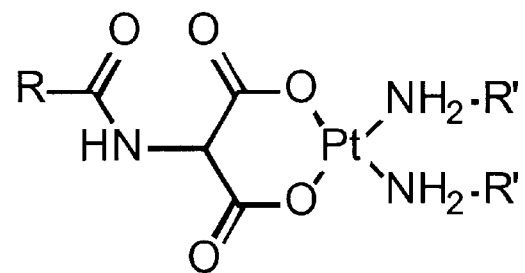
FIG. 3A shows the structure of an O,O—Pt chelate of amidomalonate-cis-diamineplatinum(II).
Figure 3B:
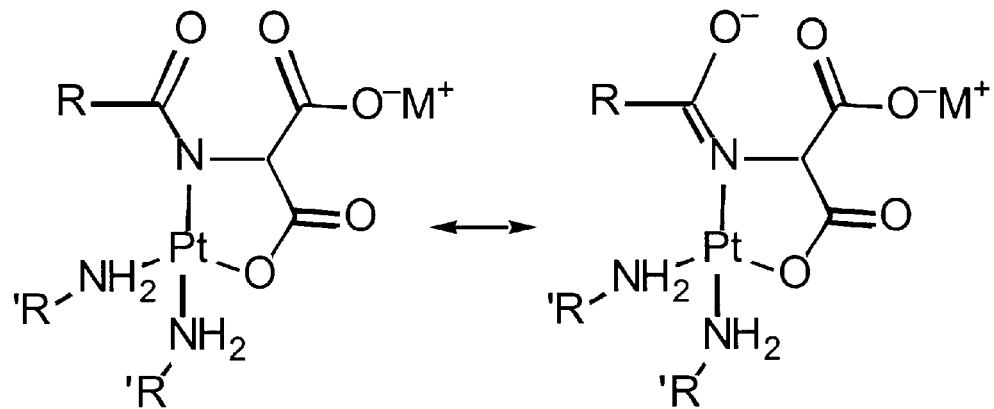
FIG. 3B shows the structure of an N,O—Pt chelate of amidomalonate-cis-diamineplatinum(II).
Figure 4:
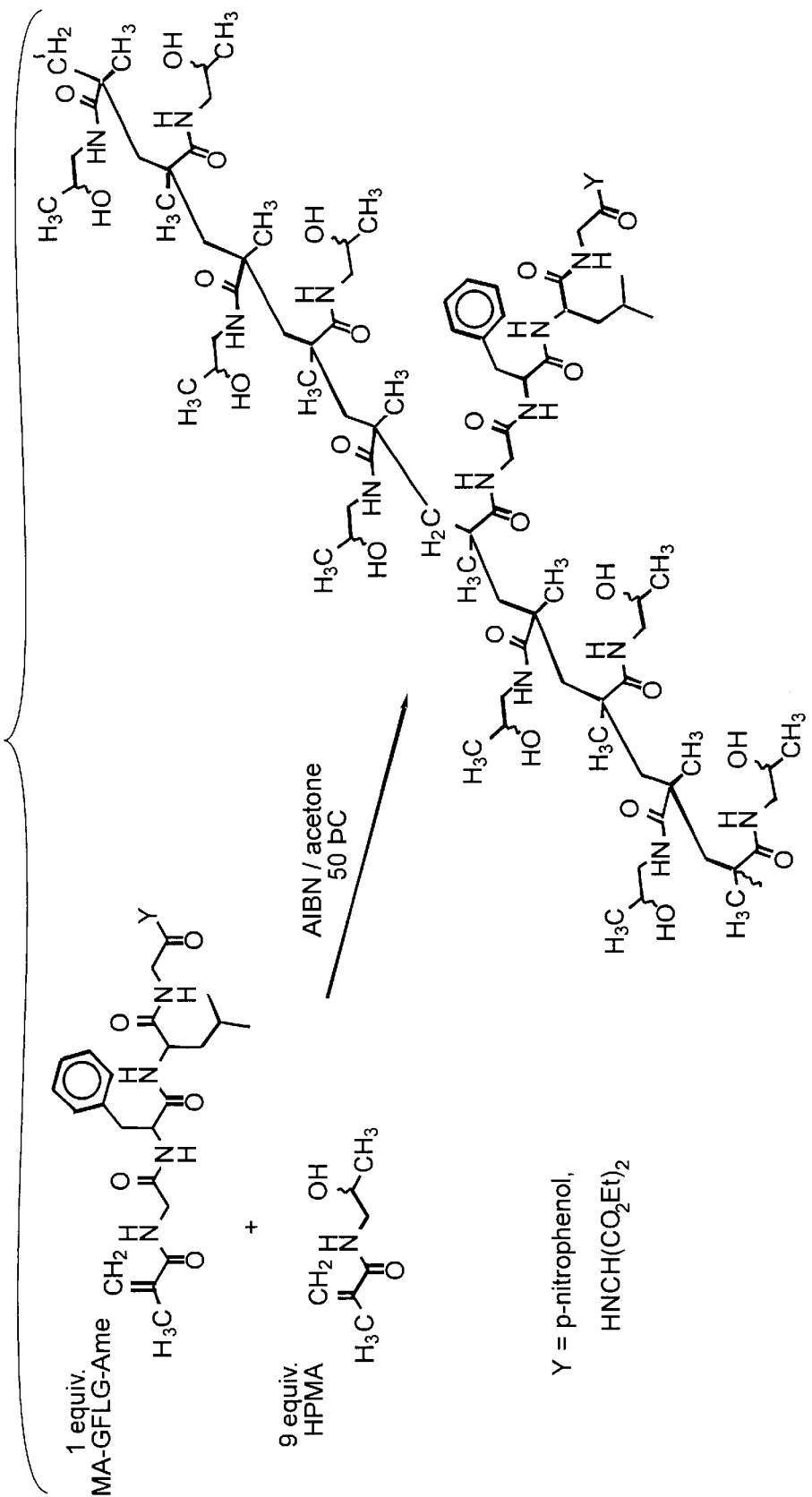
FIG. 4 shows the preparation and structure of poly(HPMA)-GFLG-Y where Y=ONp or Ama-diEt. When Y=ONp lower molecular weight polymers with narrower polydispersities are formed. Without ONp groups or added p-nitrophenol much higher molecular weight poly(HPMA) polymers are found. The 351 kDa material came from a reaction without any ONp esters and without any added p-nitrophenol. When p-nitrophenol is added to polymerization without ONp esters smaller HPMA polymers are obtained with narrower and more uniform molecular weight distributions.

The amines of the inventive N,O-amidomalonate diamine platinum(II) species can be the same or different. For the present invention amines may be $NH_3$, (i.e. ammine) primary, secondary, and tertiary amines. The amines can be heterocyclic and/or aromatic. FIG. 3b shows a such a complex with two primary amines if R' is an alkyl or aryl group; if R' is H it would be a $NH_3$ or an ammine. The two amines can be distinct entities or two parts of a single entity. The two or three R groups of secondary and tertiary amines, respectively, can be the same or different be a n-alkyl, branched-alkyl, cycloalkyl, aryl, combinations of these and other similar groups known to those with skill in the art. Also, the alkyl groups of the amines and the amines may also have other function groups provided they are compatible with platinum complex. Such compatible groups would include alcohol, ether, quaternary amine, halides, aldehyde, ketone, carboxylic acids sulfonic acids, tertiary amides, esters, and other functional groups known to those skilled in the art. Incompatible functional groups may include thiols, thioethers, etc.

A particularly preferred embodiment of the N,O-amidomalonate-diamineplatinum(II) composition is one where the two amines are each $NH_3$ moieties. Another preferred embodiment is one where the two amines are the primary amines of a 1,2-diaminocyclohexane. Particularly preferred is the trans-1R,2R-diaminocyclohexane stereoisomer (Noji, et al. 1981).

In another important embodiment, the present invention is used to treat platinum sensitive neoplasia by administration of a purified N,O-amidomalonate-diamineplatinum(II) complex to a patient. The dose may be administered IP, IV, or orally with the IP and IV routes preferred. It may be dissolved in water, isotonic fluid, or some other media suitable for administration to a patent.

An important aspect of the present invention teaches how the purity and identity of the inventive N,O-amidomalonate diamine platinum(II) complex and related complexes can be determined. Such determinations of purity and identity are necessary for a pharmaceutical product to ensure safety and efficacy. Central to the determination of identity and purity is NMR spectroscopy of $^1H$ and $^{195}Pt$ nuclei. From $^1H$ NMR spectra small hydrogen containing impurities can be seen and identified at levels down to 0.05% (wt/wt). The identity of the complex can be partly confirmed by $^1H$ NMR spectroscopy as well. For instance many examples list the proton peaks with assignments of poly(HPMA)-GFLG-Ama=Pt$(NH_3)_2$ preparations. Additionally, the O,O- and N,O—Pt chelates may be distinguished from the presence of a peak between 5 ppm and 6 ppm. The peak appears near 5.8 ppm and 5.2 ppm for the O,O- and N,O-chelates, respectively. The identity of the exact nature of the platinum complex is best determined by $^{195}Pt$ NMR spectroscopy for the chemical shift of the platinum resonances are very sensitive to its ligands and their arrangement. For O,O- and N,O—Pt chelates of amidomalonate cis-diammineplatinum(II) the resonances appear at −1733 and −2055, respectively, analogs the corresponding resonances appear at about −1850 to −1900 and −2350 to −2400 ppm, respectively. Also, other unwanted platinum species can be seen and identified. For instance, the spectrum of the O,O—Pt chelate of poly(HPMA)-GFLG-Ama=Pt$(NH_3)_2$ in Example 3 shows the presence of two other platinum peaks.

Other analytical techniques supplement and confirm the NMR spectra in regards to identity and purity. From elemental analyses the amount of platinum, sodium, chloride, and phosphate is found. [The actual results fit the expected ones with about 9% Pt and very little to no chloride or phosphate. For sodium the N,O-chelate is found to have the expected amount of 1.0% Na. The O,O-chelate has almost no sodium.] Karl-Fisher titration is used to determine water for the final product is often lyophilized. The size of the polymer and its molecular weight distribution is determined by analytical SEC. The amount of free small molecule platinum species and the amount of platinum released in physiological conditions (i.e. PBS 37° C.) is determined for free platinum species can led to higher than desired toxicities. For instance, the O,O—Pt chelates described here release much more small platinum species than the N,O-chelates. Correspondingly, the O,O—Pt chelate is much more toxic in vivo than the N,O—Pt chelate of the invention.

Another aspect of the invention teaches that the inventive platinum complex is purified to a level suitable for administration in humans. Care was taken to incorporate several sterile filtrations and use a sterile environment at critical steps along the entire process (see FIG. 5). This helps to ensure a sterile final product of the invention. The level of impurities are reduced to pharmaceutically acceptable levels by ultrafiltration. This was confirmed by analysis of the final product for chloride, phosphate, and ultrafilterable platinum. As shown by several examples, the levels of such salts and small platinum species were very low and well within necessary purity levels. Also the purification during TFF was confirmed by analyzing the permeates for platinum phosphorus and chloride.

Figure 7:
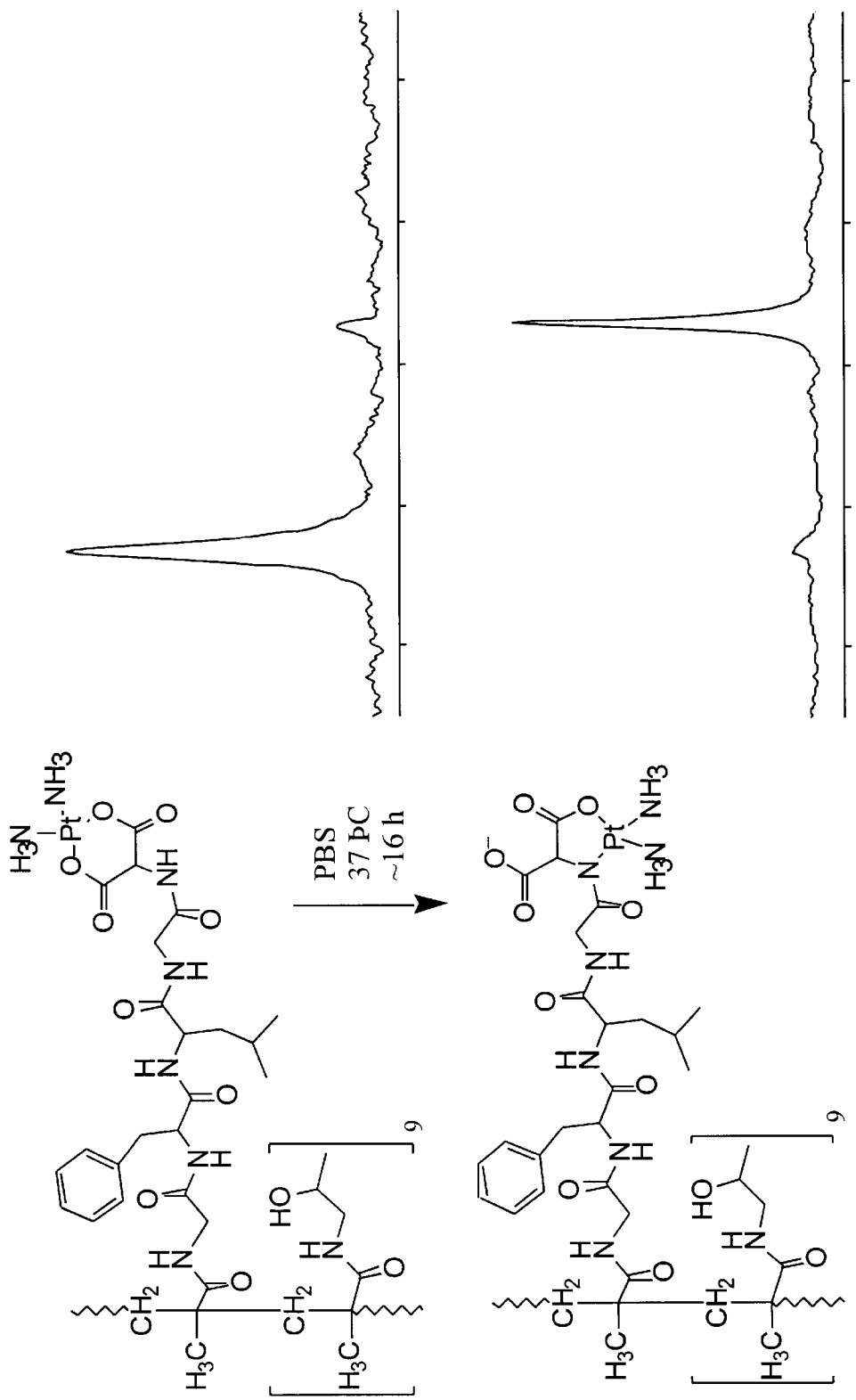
FIG. 7 shows the structures of the O,O- and N,O-chelates of poly(HPMA)-GFLG-Ama=Pt$(NH_3)_2$ with their corresponding $^{195}$Pt NMR spectra. These spectra graphically show the chelate conversion and the difference in the peak positions of the two chelates. The spectrum of the O,O- chelate shows it to consist of about 85% O,O- and 15% N,O-chelates. The spectrum of the N,O-chelate shows it to consist of about 10% O,O- and 90% N,O-chelate. If higher temperature was used or longer reaction times none of the O,O-chelate would be detectable.

A particularly important aspect of the invention teaches how the O,O- to N,O-chelate conversion does and does not occur. A comparison of the results of experiments D and E shows that higher temperatures alone are do not effect the chelate conversion, for in experiment D no significant chelate conversion occurred while in experiment E complete conversion to the N,O chelate occurred. Both of these reactions were heated to for the same amount of time. Only the one with NaCl and phosphate buffer showed the chelate conversion. This chelate conversion is shown graphically in FIG. 7. As can be seen by this figure there is still some O,O—Pt chelate remaining after 16 h in PBS at 37° C. If higher temperature and/or longer exposure time was used, no O,O—Pt chelate would be detected. A comparison of the results obtained in experiments E and F reveal that higher temperatures increase the rate of chelate conversion, for after 5 h at 50° C. the conversion was complete while after 16 h at 37° C. some O,O-chelate still remained. Experiments F and G show that pH is important for after 16 h at 37° C. at similar ionic strength and temperature, the material exposed at lower pH contained more O,O-chelate than the one at higher pH. Finally, experiment H shows that the influence of a small concentration of buffer alone allows chelate conversion to occur.

Another teaching of the inventions shows that a certain minimum concentration of NaCl is needed for efficient conversion of the O,O- to the N,O-chelate of amidomalonate-diamineplatinum(II) complexes. As indicated by FIG. 10 the chelate conversion did not proceed as far as when higher NaCl concentrations were used. (It should be noted that 10 mM phosphate buffer was used. Recognizing that phosphate can effect the chelate conversion as well higher concentration of phosphate are used to effect the preparative chelate conversion.)

Another important aspect of the present invention shows that salts other than NaCl and phosphate can effect the chelate conversion. FIG. 11 shows that a variety of anions such as nitrate, acetate, and iodide all effect the chelate conversion. Iodide, a good but labile ligand for platinum, showed the most chelate conversion at a given time, while acetate showed the least. Interestingly, nitrate (a poor ligand for platinum) effected very efficient chelate conversion.

These results are useful for NaI is soluble in many organic solvent, so it could be used to effect the chelate conversion in nonaqueous chelate conversion. On the other hand, high concentration of nitrate could be used to effect the chelate conversion in systems where other undesired ligands could chelate. The chelate conversion proceeded smoothly in bicarbonate buffer as well. It is expected that other salts of other metals, bromide, sulfate, sulfonate, etc would also effect the chelate conversion.

In one useful aspect of the invention platinum in a 4+ oxidation state forms the core of the inventive complex instead of the 2+ state. Inventive complexes with the higher oxidation may be useful for they are substitutionally inert. Thus inventive platinum complexes in the 4+ state could be prepared that may otherwise react with another part of the molecule or an undesired biological target. Additionally, platinum complexes in the 4+ oxidation state have been used for oral administration of platinum chemotherapeutics. The synthesis of the 4+ complexes would be from the corresponding 2+ complex upon oxidation with peroxides, peracid, halides, and other reagents known to those skilled in the art.

As shown by FIG. 10 NaCl concentrations at >123 mM have no significant effect on the rate of chelate conversion. However, at 60 mM NaCl the extent of chelate conversion was not as complete. This indicates that other ions, especially anions, may play a role in the rate of chelate conversion.

The results indicate that the $IC_{50}$ values for the 25 kDa O,O—Pt chelate (0.8–1.0 $\mu$M Pt) and the 25 kDa N,O—Pt chelate (3.4 $\mu$M Pt), as well as those of cisplatin (0.5 $\mu$M Pt) and carboplatin (2.4 $\mu$M Pt), fall in the same low-micromolar concentration range. This demonstrates that all of these agents display a similar cytotoxic potential to inhibit proliferation of B16F10 melanoma cells, as shown by this in vitro assay. This assay further illustrates that this cytotoxic potential is retained as the molecular weight of the polymer is increased substantially, as the $IC_{50}$ values of both the 45 kDa O,O—Pt chelate (1.0 $\mu$M) and the 90 kDa O,O—Pt chelate (0.9 $\mu$M) also fall within this low range. Thus, it would be predicted that the corresponding N,O—Pt chelates of the higher molecular weight analogs would retain their high in vitro cytotoxicity. By contrast, this assay shows that the cytotoxicities of the non-platinated higher molecular weight polymers are very low (comparable in magnitude to the control value). These data illustrate the utility of this in vitro system to routinely screen newly-produced analogs for retention of a high cytotoxic potential prior to more involved in vivo evaluation.

In one preferred embodiment of the invention, the binding of platinum to substituted HPMA carriers covering a wide distribution in molecular weight confers to these carriers substantial cytotoxic activity in a representative mammalian tumor cell system equal to or greater than that possessed by conventional antitumor platinum agents (Table 3). By contrast, substituted HPMA carriers also covering a wide distribution in molecular weight are devoid of such cytotoxic activity (Table 3). One preferred aspect of the invention is further broadly demonstrated in that such said cytotoxic activity is desirably conferred by a wide variety of platinum complexes, in part consisting of O,O-, N,O-, and DACH-linked platinum moieties attached to said representative substituted HPMA carriers having said wide distribution of molecular weights.

In one preferred embodiment of the invention, conversion of the representative O,O—Pt chelate to the preferred N,O—Pt chelate unexpectedly and desirably confers to said representative N,O—Pt chelate a marked enhancement in toleration, thereby desirably enabling the systemic administration of a markedly higher dose of the therapeutic antitumor platinum moiety (Table 4).

In one preferred embodiment of the invention, a markedly advantageous therapeutic index is achieved by means of the binding of a representative platinum complex to a polymeric carrier (substantially lower systemic toxicity of the N,O—Pt complex administered at 17.5 mg Pt/kg) compared to the conventional agent (cisplatin at 3 mg/kg), wherein both treatment regimens afford an identical degree of tumor growth reduction compared to the growth of the saline control group (FIG. 12).

The results depicted in FIG. 13 further demonstrate one preferred aspect of invention, in which antitumor activity is broadly expected to result from therapeutic platinum complexes linked to polymeric carriers. In this example, the activity of the representative O,O—Pt chelate is illustrated to yield tumor growth inhibition relative to the tumor growth of the saline control group. The growth inhibition afforded by said O,O—Pt chelate is markedly less pronounced than that of the conventional cisplatin therapy. Taken together with the more favorable tumor growth inhibitory activity afforded by the N,O—Pt chelate illustrated in FIG. 12, the unexpectedly pronounced activity of the N,O—Pt chelate relative to that of the O,O—Pt chelate is strongly demonstrated.

In one preferred embodiment of the invention, a strong and unexpected therapeutic advantage is conferred by said N,O—Pt chelate in tumor growth inhibitory activity by comparison to the representative conventional platinum agent (cisplatin), both administered at the maximum tolerated dose for a daily×5 (qd×5) regimen (FIG. 14).

In one preferred embodiment of the invention, the said N,O—Pt chelate was strongly shown to confer a wide and unexpected range of tumor growth inhibitory activity in a human squamous cell xenograft (FIG. 15) relative to the substantially different B16 melanoma model of previous examples (FIGS. 12–15). In this representative human xenograft model, said N,O—Pt chelate afforded activity at 65 or 400 mg Pt/kg equivalent to the strong activity afforded by the conventional platinum agent (carboplatin) relative to the tumor growth of the isotonic glucose control group. In one further preferred aspect of the invention, substantially less systemic toxicity is observed at the dose of 65 mg Pt/kg for said N,O—Pt chelate relative to the toxicity that results from administration of carboplatin at 65 mg Pt/kg, or that results from administration of said N,O—Pt chelate at the higher dose of 400 mg Pt/kg.

Definition of Terms

The term 'purified' refers to an complex in which ≧95% of platinum is present in one chemical form, and that other undesired material, such as reactants, chelates of metals other than platinum, by-products, salts, free ligands, and/or decomposition products (if any) have been reduced to a total of not more than 1% (wt/wt) and where any one such impurity not more than 0.5%. For administration of the purified platinum complexes to animal or human subjects for the purpose of treating cancer, the purified platinum complexes maybe formulated with approved pharmaceutical excipients and materials that are generally regarded as safe to provide stable and pharmaceutically-acceptable formulations of said purified platinum complexes.

A therapeutically effective amount is an amount causing tumor regression. It is expected to be from 1 mg/kg to 1 gm/kg body weight.

The term acrylamide polymer includes polyacrylamides and polymethacrylamides.

The term 'complex' indicates a species where a central metal atom is surrounded by ligands.

Chelate refers to ligands which form a ring with the metal atom of a complex.

The term 'ammine' refers to $NH_3$, while the term 'amine' includes $NH_3$, primary, secondary, tertiary amines be they aliphatic, aromatic, and/or heterocyclic.

The term 'Ama' of refers to aminomalonate or amidomalonate depending on context. The term 'amidomalonate' refers to an amide of 2-aminomalonic acid. It can be as the acid or salt forms.

A group 'useful for targeting' an inventive complex to a tumor is one which delivers more of the active drug to the tumor than other tissues. Such targeting includes passive targeting obtained by the EPR effect or active targeting as shown by conjugates to antibodies, lectins, folic acid, etc.

The phrase 'polymer-bound N,O-amidomalonate-diamineplatinum(II) complex refers to an inventive complex that is covalently attached to a polymer. The 'cation' of claim 4 refers to H+, alkali, alkali earth, and ammonium cations. The term 'amino acid' includes natural and unnatural alpha amino acids and amino acid such a beta alanine, 4-aminobutyric acid, 6-aminocaproic acid, p-aminobenzoic acid, etc.

The term 'proximal end' refer to the end of the oligopeptide linker that is not connected near the polymer backbone.

Folic acid derivatives are conjugates of folic acid and another molecule of interest such as an inventive complex. A folate analog is a part of close chemical relative of folate such as methotrexate, amethopterin, and pterin carboxylate.

The phrase 'side chain of a polysaccharide' refers to functional groups useful to form an amidomalonate or as part of a link to an amidomalonate. Carboxylates, amines and even hydroxy groups may be used to attach an amidomalonate for those skilled in the art. One or more platinum complexes may be bound to each polysaccharide via the side chains.

The term 'poly(Glu)-Ama-diEt indicates a polymer in which only a fraction (i.e. 15%) of the carboxyl side chains have been substituted by Ama-diEt groups. Similarly, the term poly(Glu)-Ama=Pt$(NH_3)_2$ indicates an O,O- or N,O-amidomalonate platinum chelate where all or most of the Ama groups are coordinated to a cis-diammineplatinum(II).

The term 'poly(Glu-Ama-diEt) refers to a polymer where all the carboxyl side chains have been substituted by Ama-diEt groups. The term 'poly(Glu-Ama)=Pt$(NH_3)_2$ indicates an O,O- or N,O-amidomalonate platinum chelate where only a portion (i.e. 10%) of the Ama groups are coordinated to a cis-diammineplatinum(II) species.

Abbreviations

Ama, aminomalonate or amidomalonate;

Ama-diEt, diethylaminomalonate or diethylamidomalonate;

AP5280, is the designation of the poly(HPMA)-GFLG-Ama=Pt$(NH_3)_2$ N,O-chelate 25 kDa material;

DACH, diaminocyclohexane;

DCC, dicyclohexylcarbodiimide;

DMAP, N,N-dimethylaminopyridine;

DMF, dimethylformamide;

EDC, 1-(3-dimethylamninopropyl)-3-ethylcarbodiimide hydrochloride;

FID, free induction decay;

HOBt, hydroxybenzotriazol;

HPA (2-hydroxypropylamine);

MA, methacroyl;

MTD, maximum tolerate dose, the highest dose evaluated in which no deaths resulted from drug-induced toxicity;

N,O—Pt, amido, carboxy chelate;

O,O—Pt, dicarboxy chelate;

ONp, p-nitrophenol ester;

poly(HPMA)-GFLG, copolymer of HPMA and the methacrylamide of gly-phe-leu-gly;

RCF, relative centrifugal force,

TFF, tangential flow filtration.

MATERIALS AND METHODS

I. Chemicals

Cisplatin, pyridine, ethanol, ethyl acetate, diethyl ether, diethylaminomalonate HCl salt, diethyl N-acetamidomalonate, $AgNO_3$, NaOH, 1R,2R-diaminocyclohexane, polyglutamate-Na salt, KI, PBS mixture were supplied by Sigma-Aldrich USA. The solvents were HPLC grade and reagents of ACS grade or better quality. The ion exchange resins, AG 501-X8(D) H+, HO− forms, AG 50W-X8 H+, and Chelex 100 Biotech grade, were supplied by Bio-Rad Laboratories. Class 1 water was supplied in house from a Milli-Q water system. The $K_2PtCl_4$ was supplied by All-Chemie Ltd., Mt Pleasant, S.C. The filter-aid 289 pulp was from Schleicher and Schuell. The poly(HPMA)-GFLG-ONp, poly(HPMA)-GFLG-Ama-diEt 45 kDa, and poly(HPMA)-GFLG-Ama-diEt, 351 kDa were synthesized by Polymer Laboratories, Shropshire, UK. Amino acid analysis and MALDI-TOF-MS were performed by Peptide Technologies Corp. Gaithersburg, Md.

II. Apparatus and Instrumentation

Depending on the scale 0.2 μm sterile filtrations were performed with either a 25 mm Whatman GD/X PVDF syringe filter, a Steritop media bottle filter with a GP Express membrane from Millipore, or a Millipak inline filter with a PVDF membrane from Millipore. A laminar flow hood with UV light was used for sterile operations. The pH was measured with a Beckman Phi-34 pH meter with a gel electrode calibrated at 4 and 10. Static electricity in lyophilized solids was neutralized by a Zerostat gun from Aldrich as guided by an electrostatic field meter from SIMCO, Hatfield, Pa. Platinum was analyzed by ICP-OES using a Jobin Yvon JY24 spectrometer on samples and standards diluted to 30–60 ppm in 3% $HNO_3$. Water was determined by Karl Fisher titration using an Aquastar C2000 from EM Science. Elemental analysis for Na, Cl, and P were performed by Desert Analytics, Tucson, Ariz. The $^1H$ NMR spectra were obtained on a 400 MHz Unity/Inova system from Varian, Inc. The $^{195}Pt$ NMR spectra were obtained on a 300 MHz Mercury system from Varian. Lyophilizations were performed on a Freezemobile 12EL from Virtus.

II. Aliquot Purification for Percent O,O- and N,O-Chelates

The percent of the O,O- and N,O-chelates in timed aliquots of reactions mixtures were determined by removing enough of the reaction mixture (4–15 mL depending on concentration) to give about 100 mg if only $^{195}Pt$ NMR spectroscopy was to be done or about 200 mg if, % Pt, and % water were also to be determined. The aliquots were purified by ultrafiltration using a Centricon Plus-20 centrifugal filter with a 5 kDa Biomax membrane from Millipore. The charged device was spun at the recommended RCF until about <0.5 mL remained. The reported time for the aliquot is the moment the first centrifugation was started. The filtrate was discarded, the retentate was diluted with 15–18 mL of water, and the sample was centrifuged as before. This was repeated once more, and the retentate was lyophilized to give the sample for the analyses. This technique was also used for purification of reactions of 0.1–2 g involving polymers with amidomalonate groups.

III. Platinum Release from PBS

The percent of small platinum species released over time was measured by accurately weighing and dissolving about 30 mg polymer platinum conjugate in 15 mL of phosphate buffered saline (10 mM phosphate, 123 mM Cl⁻) and incubated at 37° C. in a water bath. At indicated times 2.0 mL aliquots were transferred to a centrifugal filter with a 3 kDa nominal molecular weight cutoff (Centricon YM-3 from Millipore) and immediately spun until >1.5 mL of filtrate had accumulated. These timed filtrates and the original solution were analyzed for platinum by ICP-OES. The percent of small Pt species present at the time was determined by the formula: (ppm Pt in filtrate/ppm Pt in stock solution.)* 100.

IV. Size Exclusion Chromatography

N,O—Pt chelates were analyzed on an SEC system consisting of an HPLC instrument equipped with two PL Aquagel-OH Mixed 8 gm columns (from Polymer Labs) in column ovens at 35° C. and an RI detector. The mobile phase, consisting of a 35/65 mixture of MeOH/$H_2O$ with 10.0 mM $LiClO_4$, was pumped at a flow rate of 1.0 mL/min. Each analysis required 30 min. The column was calibrated with PEO/PEG standards and results were fit to a $4^{th}$ order polynomial of $log(M_p)$ as a function of reciprocal retention time. The reported values for $M_w$, and $M_n$ represent the average of three determinations of 100 μL of a 2 mg/mL sample dissolved in the mobile phase. O,O—Pt chelates and poly(HPMA)-GFLG-Ama-diEt were analyzed according to the method of Mendichi et al. 1996.

V. Tangential Flow Filtration.

At scales larger than about 2 grams O,O—Pt and N,O—Pt chelates of polymers were purified by tangential flow filtration (TFF) using membranes with areas of 0.05–0.1 m² made of Biomax polyethersulfone with a 5 kD nominal molecular weight cutoff. Prior to filtration the system was cleaned and sanitized by pumping 0.1 N NaOH for 30–60 min at the recommended flow rate. The caustic was removed, and fresh type 1 water (Milli-Q water) was circulated until the pH of the retentate and permeate was neutral (pH<8). The permeate flow rate was measured at an inlet pressure of 2.0 bar and an outlet pressure of 0.35 bar. Fresh type 1 water from a Milli-Q system was used as the make-up water.

VI. NMR Spectroscopies $^{195}Pt$ NMR spectra were obtained from a filtered 0.70 mL solution in 93/7 $H_2O/D_2O$ in a 5 mm tube according to the method of Bancroft et al. 1990. Enough sample (80–120 mg) was used to give a solution that was about ≧50 mM in platinum. The probe was tuned for each sample. A pulse width of 90 degrees, an acquisition time of 5.12 msec, a spectral window of 100 kHz, and no delay was used. The transmitter was placed midway between the O,O- and N,O-chelates at −1896 ppm. Between 50,000 to 250,000 transients (20–90 min) were typically required to obtain a sufficient s/n ratio of >35/1. The resulting FID was increasingly left shifted until a flat baseline was obtained, a 100 Hz line broadening was applied, and a Fourier fill of 2048 was applied before processing. Integral regions were set, and the spectrum's baseline was subjected to a spline fit by the VNMR software v6. 1. The sample was referenced externally to a 100 mM sample of $K_2PtCl4$ in 95/5 $H_2O/D_2O$, 100 mM HCl at −1624 ppm. This was also used to determine the 90 degree pulse width and T1. With a 90 degree pulse, an acquisition time of 2T1 and a delay of 3T1, 128 transients gave a s/n of >30/1 for the standard sample with the 'getsn' command.

$^{13}C$ NMR spectra were acquired on the same sample used for $^{195}Pt$ NMR. An acquisition time of 0.50 sec, a delay of 3.0 sec, about 70 degree pulse width, and 5000–10000 transients were collected to which a 3.5 Hz line broadening was applied. A s/n of >100 was typically obtained. Aqueous samples were referenced externally to 1,4-dioxane in 93/7 /$D_2O$ at 67.19 ppm. Other samples were referenced to the solvent peak.

$^1H$ NMR spectra were referenced to TMS or TMSP and acquired with standard parameters. Presaturation of the HOD signal was often used. Coupling constants (J) are in Hertz.

EXAMPLES

The following examples further illustrate embodiments of the present invention including preferred versions and methods of making the same; however these examples are not to be construed as limitations of this invention.

EXAMPLE 1

Preparation of poly(HPMA)-GFLG-Ama-diEt, About 25 kDa

Figure 1:
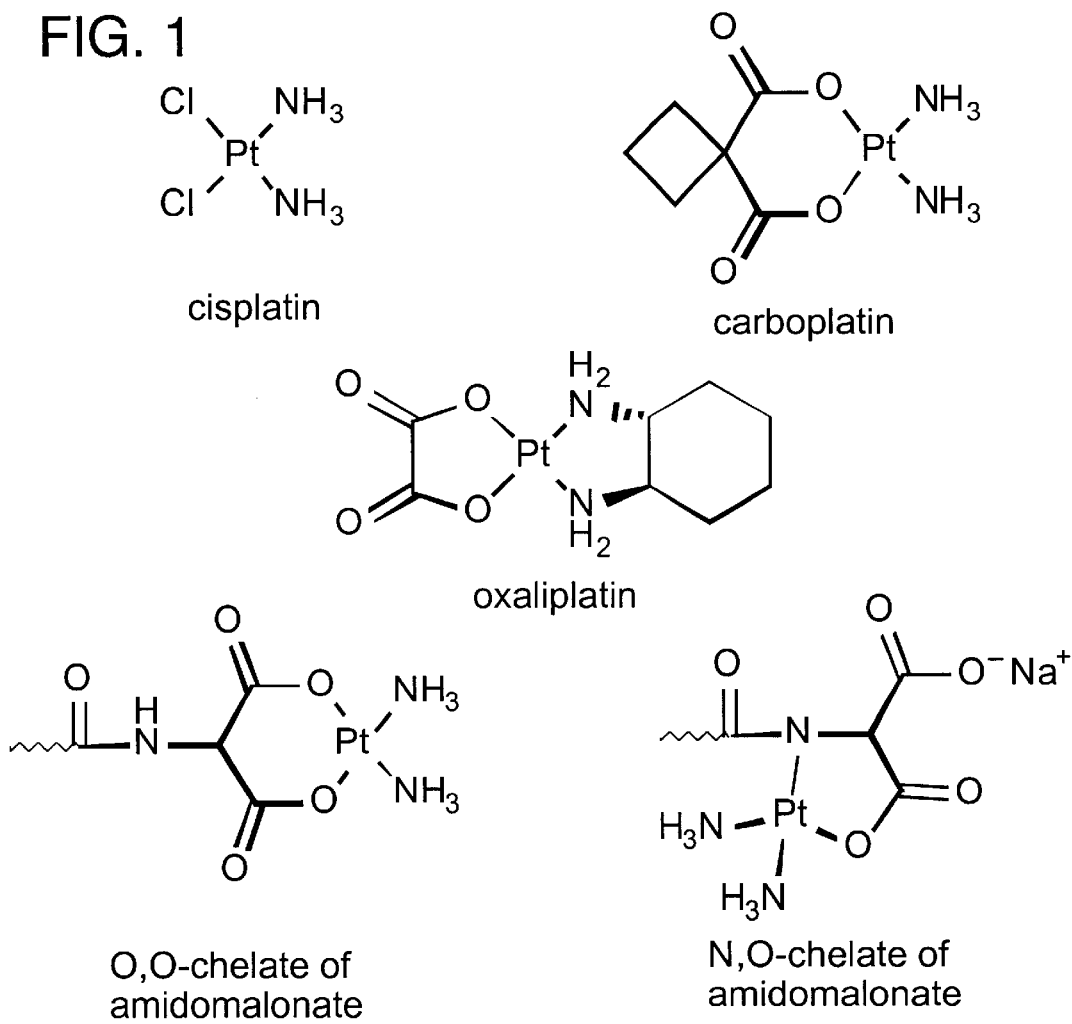
FIG. 1 shows the structures of cisplatin, carboplatin, oxaliplatin, and the the basic structures of O,O— and N,O—Pt chelates of amidomalonate-cis-diammineplatinum (II). (Note: cisplatin is also known as cDDP and cis-diamminedichlorocplatinum(II)).
Figure 2A:
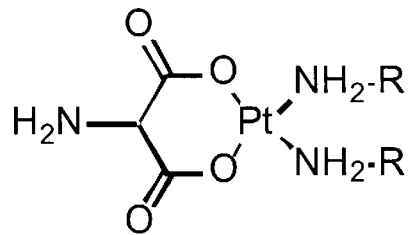
FIG. 2A shows the structure of an O,O—Pt chelate of aminomalonate-cis-diamineplatinum(II).
Figure 2B:
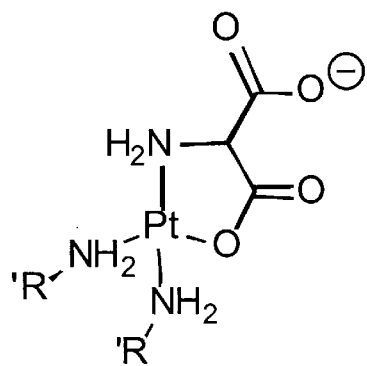
FIG. 2B shows the structure of an N,O—Pt chelate of aminomalonate-cis-diamineplatinum(II).

An oven dried 1 L round bottom flask with magnetic stir bar was fitted with a septa and cooled under vacuum. Once cooled nitrogen was introduced, the septa was removed and 29.79 g (140.8 mmol) of diethylaminomalonate HCl salt was added. The septa was replaced and 800 mL of anhydrous pyridine was cannulated into the flask. After dissolution one third of the 50 g of poly(HPMA)-GFLG-ONp (Compound I FIG. 1A of U.S. Pat. No. 5,965,118) was added. When nearly dissolved, the next third of the 50 g of ONp-polymer was introduced as described above. This procedure was repeated until all 50 g of the ONp-polymer had been added.

Figure 6:
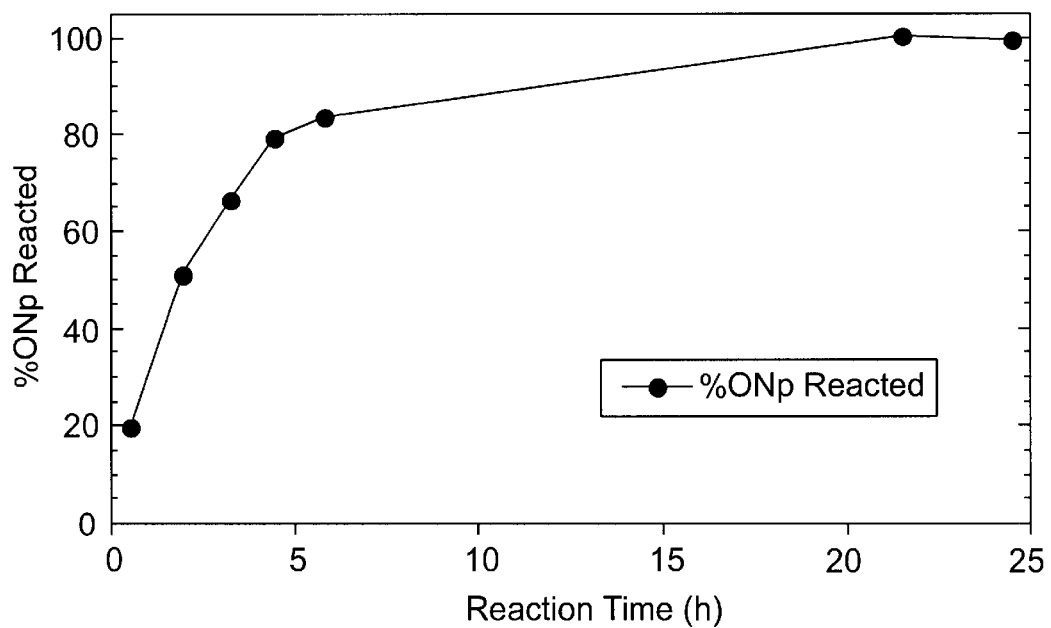
FIG. 6 shows the release of p-nitrophenol during preparation of poly(HPMA)-GFLG-Ama-diEt. This shows one way in which the substitution reaction was monitored with a small molecule.

The extent of reaction was monitored by an HPLC assay for free and total p-nitrophenol using a C18 column, UV detection at 316 nm, and a pH=4.5 /MeCN mobile phase. Aliquots were analyzed for free ONp and total after base hydrolysis (pH=12, 5 min). After 20–24 h while stirring at about 23° C. the reaction was found to be complete as shown in FIG. 6.

The reaction mixture was heated at 40–45° C. in a water bath for 3 h, cooled to ambient temperature, and the pyridine was removed in vacuo at <40° C. The residue was dissolved in abs. EtOH to give a 25% wt/vol. solution. The crude product was precipitated with 2.5 L of dry EtOAc and 0.5 L of diethyl ether. The mixture was stirred for 3–5 h then filtered through a medium glass frit. The residue was washed three times with >100 mL of ether and dried under a rubber dam to give 57–59 g. of a pale yellow solid. This solid was dissolved in 500 mL of EtOH and 3.1 g of AG 501-X8(D) IX resin (H⁺ & ⁻OH forms) per gram of filter cake was added. The mixture was stirred gently for 2.5 h, then filtered to remove the resin. The volume of EtOH was reduced to a 25% (wt/vol.) solution and precipitated as above. The pure product was collected and washed as above to give 45–46 g (about 90%) of pale yellow solid. An $^1H$ NMR spectrum of this material showed that it contained peaks characteristic of the Ama-diEt group and no small molecules except for <1% each of EtOH and EtOAc (Pinciroli, et al. 1997): Amino acid analysis (molar ratio of gly:HPA:leu:phe): 3.1:7.1:1.0:1.2; $^1H$ NMR ($D_2O$) δ 7.2–7.4 (br s, 5, ArH), 4.66 (br s, 1, α-H-phe), 4.31 (br s, 5, α-Hleu, & $OCH_2CH_3$), 4.1–3.8 (tall s and short m, ~13, —$NHCH_2CH(OH)CH_3$ and —$NHCH_2CO_2$—) 3.3–2.9 (m, —$NHCH_2CH(OH)CH_3$ and phe-$CH_2$), 2.25–1.2 (m, —$CH_2$— of polymer backbone, $CH_2$ & CH of leu), 1.20 (br s, ~31, —$NHCH_2CH(OH)CH_3$, and —$OCH_2CH_3$), 0.99 (s, $CH_3$— of polymer backbone), 0.93 and 0.87 (sh and s, 6, leu-$CH_3$).

EXAMPLE 2
Preparation of Cis-diamminediaquaplatinum (II) Dinitrate

A suspension of cisplatin (8.996 g, 29.98 mmol), $AgNO_3$ (9.959 g, 58.62 mmol), 3–5 drops of 5% $HNO_3$, and 190 mL of water were stirred overnight at about 23° C. in a foil covered low actinic media bottle then heated at 60–65° C. for 3.5 h. After cooling, to ambient temperature the mixture was filtered through a 0.22 μm filter. Its pH was about 2. A Pt and Ag analysis (ICP-OES) showed that it typically contained about 15,000–25,000 ppm of Pt and 4–14 ppm of Ag. Each preparation was analyzed for Pt, and just prior to use it was heated to 55° C. for 5 min then cooled to ambient temperature.

A preparation of the di-$^{15}$N isotopomer of cis-diammineidaquaplatinum(II) dinitrate showed a $^{195}$Pt NMR triplet at -1582 ppm which closely matches the literature value of -1580 ppm reported by Appleton et al. 1989.

EXAMPLE 3
Preparation of poly(HPMA)-GFLG-Ama=Pt($NH_3$)$_2$ O,O-chelate

1. Hydrolysis of poly(HPMA)-GFLG-Ama-diEt.

To a 1 L media bottle with a stir bar, 45 g of poly(HPMA)-GFLG-Ama-diEt (19.35 mmol Ama-diEt residues) was added to 200 mL of water. After vigorous stirring was established 135 ml water was added to give a 12–13% (wt/v) mixture. Upon dissolution in 1–2 h, 27 mL (54 mmol) of 2 N NaOH was added to raise the pH to 12.5–12.7. The pH was maintained at this range for 30 min, then 45 g of AG 501-X8(D) IX resin ($H^+$ and $^-$OH) was added. When the pH<7, the resin was removed by sterile filtration. The pH of the filtrate was raised to 7.6 with 2 N NaOH to give a solution of poly(HPMA)-GFLG-Ama-($CO_2^-Na^+$).

2. Preparation of poly(HPMA)-GFLG-Ama=Pt($NH_3$)$_2$, O,O-chelate.

To the pH=7.6 solution of poly(HPMA)-GFLG-Ama-($CO_2^-Na^+$)$_2$ of Example 3, 199 mm, of a 590.9 mM (22,940 ppm Pt) solution of cis-[Pt($NH_3$)$_2$($H_2O$)$_2$]$^{2+}$·2$NO_3^-$ prepared according to Example 2 was added in one portion to give a reaction mixture with a pH of 5.01±0.1. While stirring overnight the pH dropped to about 4.2 and a small amount of precipitate formed. After 16–18 h 17 g of Chelex 100 resin was added and stirred for 1.5 h. Before filtration about 0.5 g filter aid pulp was added and dispersed. The mixture was filtered through a coarse glass frit. An aliquot of this filtrate containing about 125 mg was removed, filtered through a 0.2 urn membrane, and purified by centrifugal ultrafiltration. The retentate was lyophilized to give about 110 mg. Alternatively, the reaction mixture can be purified by TFF as described in Example 4. $^1$H NMR $D_2O$) δ7.6 and 7.55 (br s, exchanges, NH), 7.4 and 7.3 (br s, 5, ArH), 5.9 (br s, partially exchanges, 0.2, NH-Ama) 4.65 (br s, 1, α-H-phe), 4.37 (br s,1, α-H-leu), 4.05 (sh, $NH_3$ or $CH_2$ of gly), 4.1–3.8 (tall s and short m, ~13,—$HCH_2CH(OH)CH_3$, —$NHCH_2CO_2$—)3.35–2.9 (brm, —$NHCH_2CH(OH)CH_3$ and phe-$CH_2$), 2.25–1.2 (m, —$CH_2$— of polymer backbone, $CH_2$ & CH of leu), 1.20 and 1.19 (s, ~27, —$NHCH_2CH(OH)CH_3$), 0.99 (s, $CH_3$— of polymer backbone), 0.9 (sh, 6, leu-$CH_3$); $^{13}$C NMR (93/7 $H_2O/D_2O$) δ180.1, 179.8, 179.6 175.0, 174.2, 173.3, 171.5, 171.1, 170.7, 136.6, 129.8, 129.4, 127.8, 66.5, 66.3, 59.6, 55.6, 54.7, 53.0, 47.9, 46.7, 46.0, 45.6, 43.1, 40.5, 37.8, 24.9, 23.1, 21.6; $^{195}$Pt NMR (93/7 $H_2O/D_2O$) δ-1587, -1733, -2020, and -2056 with area ratios of 1:38:1:4, respectively. Analysis shows this material to contain about 9% Pt, 5–10% water, and 0.02% Na.

EXAMPLE 4
Preparation of poly(HPMA)-GFLG-Ama=Pt($NH_3$)$_2$, N,O-chelate (AP5280)

1. O,O- to N,O-chelate conversion.

After filtration of the Chelex 100 resin from Example 3 to give about 1 L of filtrate, the solution was made 100 mM in NaCl and 75 mM phosphate (pH=7.4) by adding 5.85 g (100mmol) of NaCl, 16.35 g (61 mmol) of $Na_2HPO_4$7, and 1.93 g (14 mmol) of $NaH_2PO_4$. The pH adjusted to 7.4 with 1 N NaOH or 5% $HNO_3$. The solution was filtered and washed with buffer of the same concentration through a sterile 0.22 μm membrane into a sterile media bottle to give 1.2 L of solution and capped with a 0.22 μm membrane screw cap. This solution was warmed to 37–38° C. in a water bath, then placed at 37° C. in an oven for 22 h. At this point $^{195}$Pt NMR spectroscopy of an aliquot purified by ultrafiltration showed the platinum chelate to be ≧95% N,O-chelate and <5% O,O-chelate. (See FIG. 7).

2. TFF Purification and Lyophilization of the N,O-chelate.

The 1.2 L of N,O-chelate from above was purified by TFF as described in the methods section. The retentate, a clear dark-red solution, was sterile filtered and lyophilized to give 41.4 g (92%) of a red brown solid: % Pt=7.9±0.15%, 5.6%, 1.07% Na, <0.05% P, 0.07% Cl; $^1$H NMR($D_2O$) δ7.4 and 7.3 (br s, 5, ArH), 5.23 (br s, partially exchanged, CH of Ama), 4.65 (br s, 1, α-H-phe), 4.37 (br s,1, α-H-leu), 4.05 (sh, $NH_3$ or $CH_2$ of gly), 4.1–3.8 (tall s and short m, ~13, —$NHCH_2CH(OH)CH_3$, —$NHCH_2CO_2$—) 3.35–2.9 (m, —$NHCH_2CH(OH)CH_3$ and phe-$CH_2$), 2.25–1.2 (m, —$CH_2$— of polymer backbone, $CH_2$ & CH of leu), 1.20 and 1.19 (s, ~27, —$NHCH_2CH(OH)CH_3$), 0.99 (s, $CH_3$— of polymer backbone), 0.93 and 0.87 (sh and s, 6, leu-$CH_3$); $^{13}$C NMR (93/7 $H_2O/D_2O$) δ186.5, 185.0, 180.1, 179.9, 179.6, 176.3, 175.2, 175.0, 174.6, 174.4, 174.0, 173.9, 173.2, 171.4, 171.0, 136.6, 129.8, 129.4, 127.8, 71.0, 66.5, 66.3, 55.6, 54.7, 52.8, 47.9, 46.0, 45.6, 41.8, 40.5, 37.9, 24.8, 23.1, 21.5, 20.9, 20.7, 18.7, 17.3; $^{195}$Pt NMR (93/7 $H_2O$/$D_2O$, 64.4 MHz) δ-1733 (v br s, O,O-chelate), -2056 (s, N,O-chelate), ratio of O,O- to N,O is <5:>95, respectively; SEC $M_p$=24.5, $M_w$=24.3 kDa, $M_n$=15.7 kDa, and $M_w/M_n$= 1.55; Pt release in PBS 37° C., 0.6% at 3h, 2.0% at 24 h).

EXAMPLE 5
Formation of the O,O-Chelate

The formation of the predominately O,O—Pt chelate during the platination reaction of Example 3 was studied using the aliquot purification described above and $^{195}$Pt NMR spectroscopy. A plot of the data from one such study is shown in FIG. 8. As indicated, the reaction proceeds rapidly with a maximum amount of O,O-chelate of 90% at 1 h. As the reaction proceeds the amount of O,O-chelate decreases and the amount of N,O-chelate increases such that at 20 h there is 80% O,O-chelate and 20% N,O-chelate. Thus, if O,O-chelate material is required TFF purification (Example 4) should begin about 1 h after addition of the cis-diamminediaquaplatinum(II) cation.

EXAMPLE 6
Time Course of O,O- to N,O—Pt Chelate Conversion Under Conditions of Example 4

During the chelate conversion described in Example 4 aliquots were taken at various time intervals which were immediately purified by centrifugal ultrafiltration and lyophilized. These were subsequently freshly dissolved in 93/7

H$_2$O/D$_2$O and analyzed by $^{195}$Pt NMR spectroscopy. The peak area ratios were obtained from a spectrum at each time point which was then converted to a % N,O-chelate and plotted in FIG. 9. The composition of aliquots remained stable for at least 24 h.

EXAMPLE 7

Selective Formation of the O,O-Chelate

A method of selectively preparing the O,O-chelate was observed when the equivalents of cis-diamminediaquaplatinum(II) cation per amidomalonate group was varied. Each reaction A-C started with 2.0 g of poly(HPMA)-GFLG-Ama-diEt. Except for the number of Pt equivalents the reactions were performed as in Example 3. The reaction mixtures were lyophilized and purified by SEC using the same Sephadex G-10 column (2.5×60 cm). As shown in Table 1 when less than 1 equiv. of Pt was used, a much higher proportion of O,O-chelate was found than when 2 equiv. of platinating reagent was used.

TABLE 1

Percent O,O- and N,O- chelate formation during platination at different equiv. ofPt per Ama group.

| Reaction | Eq Pt/Eq Ama | % O,O-Chelate | % N,O Chelate | % Pt | % H$_2$O |
|---|---|---|---|---|---|
| A | 0.8 | 97 | 3 | 6.1 | 9.3 |
| B | 1.2 | 90 | 10 | 8.4 | 9.0 |
| C | 2.0 | 68 | 32 | 10.4 | 8.5 |

EXAMPLE 8

O,O- to N,O-Chelate Conversion: Effects of pH, Temperature, and Buffer

Predominately O,O-chelate material isolated from a preparation described in Example 3 and purified by TFF or SEC was subjected to variations in temperature, buffer and pH from those used in Example 4. Typically, a concentration of 10 mg/mL of the poly(HPMA)-GFLG-Ama=Pt(NH$_3$)$_2$ predominately O,O—Pt chelate was used. The results are shown in Table 2.

TABLE 2

Results from studies of temperature, buffer and pH on the extent of O,O- to N,O-chelate conversion of Example 4.

| Reaction | Time | Temp. | Buffer/pH | % O,O-/% N,O-Chelates Before Treatment | % O,O-/% N,O-Chelates After Treatment |
|---|---|---|---|---|---|
| D | 5 h | 50° C. | H$_2$O only/pH 6–7 | 78%/22% | ~80%/20% |
| E | 5 h | 50° C. | PBS$^a$/pH = 7.4 | 78%/22% | 0%/100% |
| F | 16 h | 37° C. | PBS/pH = 7.4 | 85%/15% | <10%/>90% |
| G | 16 h | 37° C. | 100 mM citrate/pH = 5.5 | 85%/15% | 16%/84% |
| H | 1:05 h | 37° C. | 10 mM phosphate/pH = 7.4 | 86%/14% | 63%/37% |

$^a$The phosphate buffered saline was 10 mM phosphate, 100 mM NaCl, and 2.7 mM in KCl.

EXAMPLE 9

O,O- to N,O-Chelate Conversion in PBS: Effect of Cl$^-$ Concentrations

The effect that various chloride concentrations may have on the rate of O,O- to N,O-chelate conversion was investigated and the results are shown in FIG. 10. About 1 g of poly(HPMA)-GFLG-Ama=Pt(NH$_3$)$_2$ predominately O,O-chelate was dissolved at 10 mg/mL in 10 mM phosphate buffer at pH=7.4 and placed at 37° C. After 1:05 h an aliquot (10 mM Phos.) was taken, and the remainder of the solution was distributed among four vessels containing enough NaCl to give 60 mM, 123 mM, 250 mM, and 500 mM NaCl. After 1.5 h (2;35 h after dissolving in 10 mM phosphate buffer) the aliquots were purified by centrifugal ultrafiltration, and the percent N,O-chelate determined by $^{195}$Pt NMR spectroscopy.

EXAMPLE 10

O,O- to N,O-Chelate Conversion in PBS: Effect of other Anions

Since the chloride anion is neither a very weak nor a very strong ligand for platinum(II) the effect of weaker or stronger ligands than chloride has on the O,O- to N,O—Pt chelate conversion were investigated. The same 10 mM phosphate pH=7.4 solution of O,O-chelate that was used in Example 9 was used to make solutions that were 123 mM in NaNO$_3$, NaOAc, and NaI. These ligands are very weak, strong and very strong ligands, respectively for platinum(II) species (Appleton, et al. 1984).

EXAMPLE 11

Preparation of poly(HPMA)-GFLG-Ama=Pt=DACH, O,O-chelate

1. Preparation of cis-diaqua-1R,2R-DACH platinum II (cis-(H$_2$O)$_2$Pt-1R,2R-DACH)

The method of Gandolfi (Gandolfi, et al. 1987) was used to prepare cis-diaqua-1R,2R DACH platinum(II). A 125 mL Erl. flask containing 3.65 g (8.79 mmol) K$_2$PtCl$_4$ and 37 mL of water were warmed to give a brown-red solution to which a solution of 5.84 g (35.2 mmol) KI in 6 mL of water was added to give a dark red solution. Upon cooling to ambient temperature 0.962 g of 1R,2R-diaminocyclohexane was added, and a yellow precipitate immediately formed. After stirring for 3 h at 25° C. the mixture was placed at 4° C. overnight. The precipitate was collected and washed with cold water, EtOH, and ether to give 4.98 g (97%) of (cis-I$_2$Pt-1R,2R-DACH)). Next, 1.00 g (1.776 mmol) of cis-I$_2$Pt-1R,2R-DACH, 0.5898 g (3.472 mmol) AgNO$_3$, and 16 mL of water were combined in a vessel protected from light and stirred at ambient temperature overnight and then at 60–65° C. for 3.5 h. Upon cooling to ambient temperature the AgCl was removed by filtration and washed once with a small amount of water. Analyses by ICP-OES of the filtrate showed that it contained 13,500 ppm Pt(69.1 mM) cis-(H$_2$O)Pt-1R,2R-DACH.

2. Preparation of poly(HPMA)-GFLG-Ama=Pt=DACH, O,O-chelate

The starting material 2.80 g of poly(HPMA)-GFLG-Ama-diEt (1.232 mmol Ama-diEt groups) was hydrolyzed and neutralized to give a pH=7.6 solution of poly(HPMA)-GFLG-Ama-(CO$_2$Na)$_2$ as described in Example 3. To this solution 1.48 mmol of cis-(H$_2$O)$_2$Pt-1R,2R-DACH dinitrate salt as an aqueous solution from above was added and stirred at ambient temperature overnight. The reaction mixture contained a precipitate which was removed by sterile filtration after addition of 0.1 g of filter aid pulp. Next, one third of the reaction was treated with 0.3 g of Chelex resin for 90 min, sterile filtered then purified by centrifugal ultrafiltration as described above. The sample was lyophilized to give 0.71 grams of a red-brown solid. 8.7% Pt, 4.2% $H_2O$; $^1H$ NMR ($D_2O$, 400 MHz) 7.7 and 7.6 (br s, ~5, NH), 7.4 and 7.3 (br s, 5, ArH), 5.86 (s, 1.6), 4.65 (br s, 1, αH-phe), 4.39 (br s,1, αH-leu), 4.1–3.8 (br m, 4, —$NHCH_2CO_2$—) 3.95 (br s, 9, $NHCH_2CH(OH)CH_3$,), 3.35–2.9 (m, 20, $NHCH_2CH(OH)CH_3$ and phe-$CH_2$), 2.6–2.3. (br s, N—CH-DACH), 2.25–1.2 (m, —$CH_2$— of polymer backbone, $CH_2$ & CH of leu, and DACH), 1.45–0.8 (br s and m, ~97, —$NHCH_2CH(OH)CH_3$, $CH_3$— of polymer backbone, leu-$CH_3$, and DACH); $^{13}C$ NMR ($H_2O/D_2O$ 93/7) δ180.0, 175.2, 174.1, 173.3, 171.8, 170.7, 136.8, 129.9, 129.5, 128.6, 128.0, 66.5, 66.3, 63.4, 55.5, 54.7, 52.8, 47.9, 46.7, 46.0, 45.6, 43.5, 40.5, 37.4, 32.4, 24.8, 23.2, 21.5, 20.9, 20.8, 18.6, 17.6, and 17.2; $^{195}Pt$ NMR ($H_2O/D_2O$ 93/7) δca. –1900 (v br s, barely perceptible, O,O—Pt=DACH, —); Pt release in PBS, 37° C.: 6.0% at 3 h, 10.9% at 24 h.

EXAMPLE 12

Preparation of poly(HPMA)-GFLG-Ama=Pt-DACH, N,O-chelate

The remaining two thirds of the reaction mixture from Example 11 was stirred with 0.6 g Chelex resin for 90 min then sterile filtered. This clear solution was made 110 mM in NaCl and 85 mM phosphate, and pH=7.4. This was kept at 37–38° C. for 22 h, then purified by centrifugal ultrafiltration and lyophilized to give 1.33 g of a red-brown solid. 8.1% Pt, 7.1% $H_2O$; $^1H$ NMR ($D_2O$, 400 MHz) 7.4 and 7.3 (br s, 5, ArH), 5.17 (s, 0.3), 4.65 (br s, 1, αH-phe), 4.38 (br s,1, αH-leu), 4.1–3.8 (br m, 4, —$NHCH_2CO_2$—) 3.95 (br s, 9, —$NHCH_2CH(OH)CH_3$,), 3.35–2.9 (m, 20, $NHCH_2CH(OH)CH_3$ and phe-$CH_2$), 2.6–2.2. (br m, N—CH—DACH), 2.25–1.2 (m, —$CH_2$— of polymer backbone, $CH_2$, CH of leu, and DACH), 1.45–0.8 (br s and m, ~100, —$NHCH_2CH(OH)CH_3$, $CH_3$— of polymer backbone, leu-$CH_3$, and DACH); $^{13}C$ NMR ($H_2O/D_2O$ 93/7) δ186.8, 185.3, 180.0, 175.1, 174.6, 174.1, 173.5, 171.5, 171.1, 136.7, 129.9, 129.5, 127.9, 70.2, 66.5, 66.3, 64.2, 63.3, 61.0, 55.6, 54.7, 52.9, 47.9, 56.7, 46.0, 45.6, 44.2, 43.3, 41.2, 40.5, 37.9, 32.7, 24.8, 24.6, 23.1, 21.5, 20.9, 20.7, 18.6, 17.3; $^{195}Pt$ NMR ($H_2O/D_2O$ 93/7) δ–2293, no peak at –1900, and no other peaks. Pt release in PBS, 37° C.: 2.0% at 3 h, 2.1% at 24 h.

EXAMPLE 13

Preparation of poly(glutamate)-Ama-diEt

The procedure of Li (Li et al. 1998) was adapted to substitute about 15% of the free carboxylates of polyglutamate. To a bottle containing 0.5 g (3.29 mmol —$CO_2$ groups) of polyglutamate and a stir bar, 104 mg (0.493 mmol) of diethylaminomalonate HCl salt, 3 mg DMAP, and 10 mL of dry DMF (HPLC grade, >48 h over 4A sieves) was added in a dry box and stirred to give a cloudy mixture. Next, 315 mg (1.36 mmol) DCC was added, a septum inserted into the mouth of the bottle, 2 mL of 1.0 M HCl in ether was added, and the mixture was stirred overnight at ambient temperature.

Afterwards, about 15 mL of $CHCl_3$ was added, and the cloudy mixture was centrifuged at 3850 RCF for 15 min. The supernatant was discarded, and the white gel material was stirred with 2.5% $NaHCO_3$ for 30 min. The mixture was centrifuged as before, and the supernatant was lyophilized to give 1.91 g of white solid whose $^1H$ NMR showed the presence of DMF, EtOH, DCC/DCU and peaks of polyglutamate and diethylamidomalonate, and diethylaminomalonate. (The peak areas at 4.3 ppm (α-CH of glu and —$OCH_2CH_3$) and 2.4 ppm (a $CH_2$ of glu) are about 1:1 where as in polyglutamate they are 1:2, respectively.) This material was dissolved in water and purified by centrifugal ultrafiltration to give 216 mg of a white solid whose $^1H$ NMR spectrum indicated the presence of DCC/DCU. Also, addition of NaOD to a solution in $D_2O$ liberated EtOH corresponding to 0.67 mmol Ama-diEt groups per gram of poly(glu)-Ama-diEt. Without further purification this was used in Example 14.

EXAMPLE 14

Preparation of poly(glutamate)-Ama=Pt($NH_3$)$_2$, O,O-and N,O-chelates

1. Preparation of the O,O-chelate of poly(glutamate)-Ama=Pt($NH_3$)$_2$

To 4 mL of water in a 20 mL vial with a stir bar, 188 mg (0.126 mmol Ama-diEt equiv.) of poly(glu)-Ama-diEt from Example 13 was added. Once dissolved the pH was raised to 12.4–12.8 for 20 min then 0.2 g of AG-50W-X8 H+IX resin was added. Within 2 min the pH fell to 6. The resin was removed by filtration through a coarse glass frit, then the filtrate was sterile filtered. The pH of the filtrate was raised to 7.1 with fresh 2 N NaOH, and 1.3 mL of a 19,000 ppm Pt solution (0.126 mmol) of cis-diamminediaquaplatinum (II) $2NO_3^-$ prepared according to Example 2 was added. This was stirred for 35 min then purified by centrifugal ultrafiltration as described above. After concentrating to 18 mL and three water washes of 15 mL each, the retentate was lyophilized to give 182 mg of a white solid whose $^{195}Pt$ NMR spectrum showed two peaks –1595 and –1732 ppm in about 1:4 ratio, respectively. The major peak at –1732 is the O,O-amidomalonate chelate of cis-diammineplatinum(II). Attempts to further purify this material gave a gelatinous mass perhaps due to crosslinking of glutamate carboxylates by cis-diammine Pt, so this material was subjected to the chelate conversion conditions of Example 4 and related examples.

2. Preparation of the N,O-chelate of poly(glutamate)-Ama=Pt($NH_3$)$_2$

The above poly(glutamate)-Ama=Pt($NH_3$)$_2$, O,O-chelate was subjected to the O,O- to N,O-chelate conversion conditions of Example 4 with the sample made 110 mM NaCl, 85 mM phosphate, pH=7.4. After about 22 h at 38° C. it was purified by centrifugal ultrafiltration and the retentate lyophilized to give 163 mg of a white solid that contained 15.5% Pt (0.77 mmol Pt/g polymer), 0.035% P; 186.9, 183.6, 182.8, 182.1(p-glu), 180.0, 175.3, 174.2(p-glu), 173.6, 172.5, 171.0, 170.7, 155.7, 72.1, 63.6, 62.7, 60.4, 25.4, 54.2(p-glu), 53.5, 51.6, 34.2(p-glu), 32.1, 31.4, 30.8, 28.6(p-glu), 26.0, 25.5, 25.0; $^{195}Pt$ NMR (93/3 $H_2O/D_2O$) δ1595 (v br s, 22%, ($NH_3$)$_2$Pt($RCO_2$) and ($RCO_2$, $H_2O$ and/or HO)) and –2053 (br s, 78%, N,O-chelate of amidomalonate).

EXAMPLE 15

Preparation of poly(glu-AmadiEt)

The procedure of Danishefsky (Danishefsky et al. 1971) was adapted to substitute every carboxyl group of polyglutamate. To a bottle containing 0.5 g (3.29 mmol of —$CO_2Na$ groups) of polyglutamate and a stir bar, 1.39 g (6.58 mmol) of diethylaminomalonate HCl salt, 1.89 g (9.862 mmol) EDC, 0.503 g (3.287 mmol) HOBt, and 20–25 mL of dry DMF (HPLC grade, >48 h over 4A sieves) was added in a dry box and stirred to give a cloudy mixture. After stirring overnight at ambient temperature the mixture was pour into 150 mL water to give a white solid precipitate. (The peak areas at 4.3 ppm (α-CH of glu and —$OCH_2CH_3$) and 2.4 ppm (a $CH_2$ of glu) are about 1:1 where as in polyglutamate they are 1:2, respectively.) This material was dissolved in water collected by filtration, and washed with water. After drying in vacuo for 3 days, 0.79 g (84%) of solid material was obtained. $^1$H NMR (CDCl$_3$) δ8.25 (v br s, 1, NH-glu), 7.24 (br s, 1, NH-Ama), 5.16 (d, 1, J=5.7, CH-Ama), 4.22 and 4.1 (m and br s, OCH$_2$CH$_3$ and CH-gly) 2.65, 2.33, and 2.18 (br s, 4, CH$_2$CH$_2$-glu), and 1.26 (br t, 6, OCH$_2$CH$_3$); $^{13}$C NMR (CDCl$_3$) δ175.9, 171.9, 166.5, 62.4, 56.8, 56.4, 32.5, 26.3, and 13.9. Without further purification this was used in Example 16.

EXAMPLE 16
Preparation of poly(glu-Ama)=Pt(NH$_3$)$_2$, O,O— and N,O— Pt Chelates About 30 mL of an EtOH slurry of 0.79 g (2.75 mmol Ama-diEt groups) of poly(glu-AmadiEt) was combined with fresh 40 mM NaOH. The pH was held at 12.3–12.6, and mixture was warmed and sonicated for 30 min. The mixture was slightly hazy. The pH was reduced to 7.26 with 1.8 g of H+IX resin, sterile filtered to give a faint yellow solution. The volume was reduced to about 30 mL in vacuo, and 4.2 mL of a 18,400 ppm Pt (0.39 mmol) solution of cis-diamminediaquaplatinum(II) dinitrate was added to give a solution with pH 5.97. This was reduced to 5.0 with 5% HNO$_3$ and stirred for 1 h at ambient temperature.

1. Isolation of poly(glu-Ama)=Pt(NH$_3$)$_2$, O,O—Pt chelate.

After stirring for 1 h a sample of poly(glu-Ama)=Pt(NH$_3$)$_2$ reaction mixture was lyophilized to give 90 mg of a white solid whose H NMR spectrum indicates that only 67% of the ethyl esters were hydrolyzed: 10.3% Pt; $^1$H NMR (D$_2$O) δ5.93 (s, 0.1 exchanged, CH-ama), 4.4–4.1 (m, 3.4, CH-glu, OCH$_2$CH$_3$, and NH3?), 2.46 (br s, 2, CH$_2$CH$_2$), 2.07 (br s, 2, CH$_2$CH$_2$), and 1.25 (br q, 2, OCH$_2$CH$_3$); $^{13}$C NMR(H2O/D$_2$O 93/7) δ175.1, 175.0, 174.8, 174.5, 173.8, 171.1, 171.0, 170.8, 170.5, 63.6, 60.7, 60.4, 60.0, 53.7, 31.9, 27.8, and 14.0; $^{195}$Pt NMR (H$_2$O/D$_2$O 93/7) 67 −1734 (O,O—Pt, 86%) and −2034 (N,O—Pt, 14%).

2. O,O— to N,O—Pt chelate conversion and isolation of poly(glu-Ama)=Pt(NH$_3$)$_2$, N,O—Pt chelate.

The remaining 32 mL of poly(glu-Ama)=Pt(NH$_3$)$_2$, O,O—Pt chelate solution was made 110 mM in NaCl, 85 mM phosphate by the addition of 207 mg NaCl, 76 mg NaH$_2$PO$_4$ 1 H$_2$O, and 588 mg Na$_2$HPO$_4$ 7 H$_2$O. The pH was adjusted to 7.4, the solution was sterile filtered, and incubated at 42° C. for 16 h. The solution was slightly hazy. It was refiltered then purified by centrifugal ultrafiltration. The retentates were lyophilized to give about 600 mg of a light yellow solid: 11.4% Pt, $^1$H NMR (D$_2$O) δ5.2 (br s, 0.1 exchanged, CH-ama), 4.59 (br s, 0.2), 4.4–4.1 (m, 2.5, CH-glu, and OCH$_2$CH$_3$), 400 and 3.85 (br s, 0.25), 2.47 (br s, 2, CH$_2$CH$_2$), 2.06 (br s, 2, CH$_2$CH$_2$), and 1.25 (br q, 2, OCH$_2$CH$_3$); $^{13}$C NMR (H$_2$O/D$_2$O 93/7) δ175.1, 174,8, 174.4, 173.7, 171.0, 170.8, 170.5, 63.5, 63.1, 62.7, 53.7, 32.2, 31.8, 27.9, 14.0; $^{195}$Pt NMR(H$_2$O/D$_2$O 93/7) δ−1730 (O,O—Pt, 8%) and −2053 (N,O—Pt, 92%).

EXAMPLE 17
Preparation of N-Acetamidomalonate=Pt(NH$_3$)$_2$ O,O- and N,O-chelates In a 20 mL vial, 800 mg (3.68 mmol) N-acetamidomalonate was stirred with 8 mL of water, and 2.0 mL of 2N NaOH. Within 3 min a faint yellow solution at pH=12.6 was obtained. After 30 min H+IX resin was added, and the pH dropped to 7.0. The resin was removed by filtration, the pH was raised to 7.5, and 25.3 mL of a 28,375 ppm Pt (3.63 mmol) solution of cis-diamminediaquaplatinum(II) dinitrate. The pH dropped to 4.4. Upon addition of 2 drops of 2N NaOH a white solid formed. The mixture was filtered, and a sample was made to 10% in D$_2$O and analyzed by $^{195}$Pt NMR spectroscopy. Only a peak at −1734 was apparent.

This filtrate was made to 100 mM in KI and 50 mM in KHCO$_3$, and sterile filtered. Its pH was 7.7–7.9. This was place at 40° C. for 18 h. An orange precipitate which formed was removed by filtration, and the filtrate stripped in vacuo. The residue was stirred with 20 mL of acetone for 1 h. A portion was filtered, made to 7% D$_2$O, and analyzed by $^{195}$Pt NMR spectroscopy. Only one peak at −2057 ppm was apparent.

EXAMPLE 18
Preparation of poly(HPMA)-GFLG-Ama-diEt, 45 kDa and 350 kDa

1. Preparation of MA-GFLG-Ama-diEt

About 25 g of MA-GFLG-ONp was treated with 1.2 equivalents of diethylaminomalonate HCl salt, 3 equivalents TEA, 1 equivalent HOBt in DMF solution at 50° C. for about 16 h. The DMF was removed in vacuo, and the residue slurried with diethyl ether and cooled to 4° C. overnight. The product was collected by filtration, washed with ether, and dried in vacuo to give MA-GFLG-Ama-diEt whose identity and purity was confirmed by $^1$H NMR spectroscopy and HPLC. $^1$H NMR (DMSO-d6) δ8.74 (d, 1, J=7.3, NH-Ama), 8.14 (t, 1, J=5.9, CH$_2$-gly), 8.11 (d,1, J=8.2, αCH leu), 8.03 (t, 1, J=8.2, CH$_2$ gly), 8.01 (d, 1, J=8.2, NH-phe), 7.3–7.0 (m, 5, ArH),5.70 (s, 1, =CH$_2$), 5.37 (t, 1, J=1.6, =CH$_2$), 5.09 (d, 1, J=7.3, CH-Ama-diEt), 4.53 (m, 1, αCH of phe), 4.32 (m, 4, OCH$_2$CH$_3$), 3.9–3.7 (m, 3, CH$_3$-gly). 3.63 and 3.59 (dd, 1, J=16,3,5.8), 3.1–3.0 and 2.83–2.73 (m,2, CH$_2$-phe), 2.51, (m, 3, J=1.7, CH$_3$—C=CH$_2$), 1.59 (m, 1, J=6.5, CH$_2$CH(CH$_3$)$_2$), 1.49 (t, 2, J=7.5, CH$_2$CH(CH$_3$)$_2$), 1.216 and 1.214 (two t, 6, J=7.2, OCH$_2$CH$_3$), 0.88 (d, 3, J=6.6, CH$_2$CH(CH$_3$)$_2$), and 0.84 (d, 3, J=6.5, CH$_2$CH(CH$_3$)$_2$).

2. Preparation of poly(HPMA)-GFLG-Ama-diEt, about 45 kD.

A vessel with condenser was charged with 12.7 wt % of HPMA and MA-GFLG-Ama-diEt monomers in a 90/10 ratio, respectively, 0.6 wt % pure AIBN, 10 mol % p-nitrophenol (of total monomers), and 86 wt % acetone. The mixture was degassed for 30 min or more with bubbled nitrogen, then heated at 50° C. for 65 h. The solid product, poly(HPMA)-GFLG-Ama-diEt was collected by filtration and washed with ether. It was redissolved in abs. EtOH at about 25% wt/vol, then precipitated with 8 volumes of EtOAc. The resulting solid was collected by filtration, washed with ether, and dried in vacuo to give about 20 g of off white powder. Its $^1$H NMR spectrum was very similar to the 25 kDa version. Mw=44.5 kDa, PDI=1.76, bimodal. Amino acid analysis: ($\mu$mol/mg polymer) 2.7:8.1:0.9:0.9 of gly: 2-hydroxypropylamine: leu:phe, respectively; MALDI-TOF-MS (NBA matrix) m/z M$^+$ 40–45 kDa, M$^{+2}$ 14–16 kDa.

3. Preparation of poly(HPMA)-GFLG-Ama-diEt, about 350 kD.

The procedure for the 45 kD batch of poly(HPMA)-GFLG-Ama-diEt was repeated except that p-nitrophenol was omitted. About 25 g of a white powder was obtained. Its $^1$H NMR spectrum was very similar to the 25 kDa version thought the peaks were broader. Mw=351 kDa, PDI=3.95, trimodal.

EXAMPLE 19
Preparation of poly(HPMA)-GFLG-Ama=Pt(NH$_3$)$_2$, N,O-chelate 45 kDa To a 250 media bottle containing a stir bar 72 mL of water and 15.5 g (6.82 mmol Ama-diEt groups) of poly(HPMA)-GFLG-Ama-diEt were respectively added. Once vigorous stirring was established 48 mL of additional water was added, and the mixture was stirred for about 1 h to give a pale violet solution. To this solution 12 mL of fresh 2 M NaOH was added, and the pH rose to 12.6. The pH was maintained at 12.4–12.8 for 30 min then 15.4 g of mixed bed IX resin (AG 501-X8(D) H+, —OH forms) was added. The pH dropped to 5.0 after 3 min and the resin was removed by filtration through a sterile Steritop 150 mL filter. The pH of the filtrate was raised to 7.60 with fresh 2N NaOH, and 8.14 mmol (64 mL, 24,200 ppm Pt) of freshly prepared diammine-diaquaplatinum(II) solution was added in one portion. After addition the pH was 5.1 and was stirred overnight. Afterwards, the pH was 4.42, and 5.10 g Chelex 100 resin was added. The pH rose to 5.33, and the mixture stirred for 90 min. The resin was removed by filtration through a coarse glass frit to give 460 mL of solution. The filtrate was made 110 mM in NaCl, 80 mM in phosphate by addition of 2.96 g NaCl, 1.08 g $NaH_2PO_4$ $H_2O$, and 7.66 g $Na_2HPO_4$ $7H_2O$. The pH was adjusted to 7.4 with 2N NaOH and 5% $HNO_3$ then steril filtered through a Steritop filter into a sterilized media bottle and affixed with a membrane cap within a biological safety hood. This was placed in a 39° C. water bath for 20 min then at 37–38° C. in an incubator oven.

After 22 h at 37–38° C. the solution was purified by TFF. The solution was concentrated to 5% wt/vol, 7 volumes of permeate were collected, then the retentate was concentrated to 8–10% when the permeate became slightly colored. The retentate was sterile filtered through a Millipak 20 filter into a sterilized lyophilization flask. After lyophilization 11.2 g (66%) of off-white solid was obtained: 8.89% Pt, 5.4% $H_2O$, 1.03% Na, 0.05% Cl, <0.05% P; $^1H$ NMR ($D_2O$) δ7.4 and 7.3 (br s, 5, ArH), 5.23 (br s, partially exchanged, CH of Ama), 4.66 (br s, 1, α-H-phe), 4.37 (br s, 1, α-H-leu), 4.05 (sh, $NH_3$ or $CH_2$ of gly), 4.1–3.8 (tall s and short m, ~13, —$NHCH_2CH(OH)CH_3$, —$NHCH_2CO_2$—) 3.35–2.9 (m, 18, —$NHCH_2CH(OH)CH_3$ and phe-$CH_2$), 2.25–1.2 (m, —$CH_2$— of polymer backbone, $CH_2$ & CH of leu), 1.20 and 1.19 (s, ~27, —$NHCH_2CH(OH)CH_3$), 0.99 (s, $CH_3$— of polymer backbone), 0.93 and 0.87 (sh and s, 6, leu-$CH_3$); $^{13}C$ NMR ($H_2O/D_2O$ 93/7) δ186.7, 71.0, and all other peaks as reported for Example 4; $^{196}Pt$ NMR ($H_2O/D_2O$ 93/7) δ–2055 (100%).

EXAMPLE 20

Preparation of poly(HPMA)-GFLG-Ama=Pt(NH$_3$)$_2$, N,O-chelate >351 kDa

To a 500 mL media bottle with a stir bar, 120 mL water and 20 g (8.80 mmol Ama-diEt) poly(HPMA)-GFLG-Ama-diEt (351 kDa) were, added, respectively. Once vigorous stirring was established 100 mL water was added, and the mixture was stirred for 2 h when all polymer dissolved to give a colorless solution. A pH electrode was inserted, and 14 mL of fresh 2 N NaOH was added. The pH rose to 12.74 and was held between 12.4–12.8 for 30 min. Afterwards, 19.9 g of mixed bed (H+, —OH forms) IX resin (AG 501-X8(D) was added, and within 3 min the pH fell to 6. The mixture was sterile filtered through a Steritop bottle-top filter, and its pH was adjusted to 7.63 with 2N NaOH and 5% $HNO_3$. In one portion 85.5 mL of a 24,200 ppm Pt solution (10.6mmol) of freshly prepared diamminediaquaplatinum (II) solution was added to give a pH of 5.02. This solution appeared slightly cloudy due to the size of the particles, and was stirred overnight at ambient temperature. During this period the pH fell to 4.25, and 6.77 g Chelex100 resin was added. The pH rose to 5.33, and after stirring for 90 min 0.2 g of filter aid pulp was added. The mixture was sterile filtered through a coarse glass frit. This solution, 725 mL, was made 110 mM in NaCl and 85 mM in phosphate by the respective addition of 4.661 g (79.8 mmol) NaCl, 12.24 g (45.7 mmol) of $Na_2HPO_4$ $12H_2O$, 1.703 g (10.1 mmol) of $NaH_2PO_4$ $1H_2O$. The pH was adjusted to 7.4 and then passed through a Steritop filter into a 1 L media bottle. This bottle was sealed with a membrane cap and placed in a water bath at 40° C. for 20 min then at 37–38° C. in an incubator oven. After about 22 h, the contents were subjected to purification by TFF as described above. NMR spectrocopies were performed with about 50 mg, for the more concentrated solution were too viscous. Lyophilization of the retentate gave 19.9 g of white solid: 7.95%Pt, 7.0% $H_2O$, 1.03% Na, 0.09% Cl, <0.05% P; $^1H$ NMR ($D_2O$) δ7.4 and 7.3 (br s, 5, ArH), 5.23 (br s, partially exchanged, CH of Ama), 4.65 (br s, 1, α-H-phe), 4.38 (br s,1, α-H-leu), 4.05 (sh, $NH_3$ or $CH_2$ of gly), 4.1–3.8 (tall s and short m, ~13, —$NHCH_2CH(OH)CH_3$, —$NHCH_2CO_2$—) 3.35–2.9 (m, 18, —$NHCH_2CH(OH)CH_3$ and phe-$CH_2$), 2.25–1.2 (m, —$CH_2$— of polymer backbone, $CH_2$ & CH of leu), 1.20 and 1.19 (s, ~27, —$NHCH_2CH(OH)CH_3$), 0.99 (s, $CH_3$— of polymer backbone), 0.093 and 0.87 (sh and s, 6, leu-$CH_3$); $^{13}C$ NMR ($H_2O/D_2O$ 93/7) δ186.7, 71.0, and all other peaks as reported for Example 4; $^{196}Pt$ NMR($H_2O/D_2O$ 93/7) δ–2055 (100%).; SEC trimodal, Mp=468 kDa, 147 kDa Mn=66.3 kDa, PDI=13.8; Pt release: 0.68% at 3 h, 2.28% at 24 h.

EXAMPLE 21

In vitro Activity of O,O- and N,O-chelate

Characterization of activity in tissue culture. The relative cytotoxic activity of various O,O—Pt chelate analogs were evaluated in vitro by means of a clonogenic (colony-formation) assay employing a tissue culture of B16F10 melanoma cells. In this way, the activity of the analogs was compared to that of cisplatin and carboplatin (active conventional platinum agents). The effect of conversion to an N,O—Pt chelate was also evaluated. Briefly, cells were seeded into culture dishes and allowed to attach. The cultures were incubated for 7 days in medium containing the desired concentration of the test agent. After fixation, the number of cell clusters containing >50 cells was scored as a colony. Each concentration of test agent was assayed in triplicate. The mean number of colonies in each of the triplicate dishes was divided by the mean number of colonies in the control (no test agent) dishes to obtain a percent survival value for each concentration of test agent. The $IC_{50}$. (concentration resulting in 50% inhibition of growth) of each of the agents was determined by performing linear regression analysis, using the data values directly above and below the 50% survival point.

TABLE 3

Cytotoxicity results from Clonogenic assays for O,O-Pt and N,O-Pt chelates of amidomalonates.

| Chelate | $IC_{50}$ value (µM) |
| --- | --- |
| Control | >300 |
| p(HPMA)-GFLG-Ama, 90 kDa O,O-Na | >100 |
| p(HPMA)-GFLG-Ama = Pt(NH$_3$)$_2$, 25 kDa N,O-Pt | 3.4 |
| p(HPMA)-GFLG-Ama = Pt(NH$_3$)$_2$ 25 kDa O,O-Pt | 0.8–1.1 |
| p(HPMA)-GFLG-Ama = Pt(NH$_3$)$_2$ 45 kDa O,O-Pt | 1.0 |
| p(HPMA)-GFLG-Ama = Pt(NH$_3$)$_2$ 90 kDa O,O-Pt | 0.9 |
| p(HPMA)-GFLG-Ama, 45 kDa O,O-Na | >100 |
| p(HPMA)-GFLG-Ama = Pt-DACH, 25 kDa O,O-Pt | 1.0 |
| p(HPMA)-GFLG-Ama = Pt-DACH, 25 kDa N,O-Pt | <4 |
| Cisplatin | 0.5 |
| Carboplatin | 2.4 |

EXAMPLE 22

Toleration and Maximum Tolerated Dose Studies

Single-dose IV studies comparing the O,O—Pt chelate to the N,O—Pt chelate forms of AP5280 (i.e. poly(HPMA)-

GFKG-Ama=Pt(NH$_3$)$_2$) have shown that the maximum tolerated doses (MTD) in mice are 80–100 and 400 mg Pt/kg for the O,O—Pt chelate and the N,O—Pt chelate respectively, indicating the increased safety margin afforded by the polymer bound N,O—Pt chelate. For these studies, the MTD was defined as the highest dose evaluated in which no mouse deaths resulted from drug-induced toxicity.

The toleration of multiple doses of both chelates, as expressed by the maximum mean body weight loss of groups of 10 mice bearing B16 melanoma tumors given five daily doses of either chelate, is shown in Table 1. These data also indicate the lack of toxicity of the N,O—Pt chelate at an equivalent dose of the O,O—Pt chelate (17.5 mg Pt/kg), and the substantially higher dose of the N,O—Pt chelate (>240 mg Pt/kg) necessary to produce an equivalent mean weight loss.

TABLE 4

Toleration of AP 5280 Expressed as Mean Percent Body Weight Reduction for Daily dosing x 5 of poly(HPMA)-GFLG-Ama = Pt(NH$_3$)$_2$, O,O- and N,O-Pt chelates, 25 kDa.

| O,O-Pt Chelate | | N,O-Pt Chelate | |
| --- | --- | --- | --- |
| Dose (mg Pt/kg) | Percent Weight Loss | Dose (mg Pt/kg) | Percent |
| 7.5 | −10.3 | 10 | +5.6 |
| 20 | −29.9 | 20 | −2.5 |
| | | 40 | −4.8 |
| | | 80 | −7.7 |
| | | 200 | −19.9 |
| | | 240 | −26.0 |

EXAMPLE 23

Tumor Growth Inhibition in a s.c. B16 Melanoma Model: N,O—Pt Chelate

Tumor growth inhibition of poly(HPMA)-GFLG-Ama=Pt(NH$_3$)$_2$, N,O—Pt chelate, 25 kDa ,N,O—Pt) versus cisplatin and saline control was evaluated in female C57BL/6 mice. The N,O—Pt chelate and cisplatin were dosed at 17.5 mg Pt/kg and 3 mg/kg, respectively on a qd×5 schedule. This N,O-chelate dose is well below its MTD, while the cisplatin dose is near its MTD. Ten animals per treatment group were inoculated s.c. in the right rear flank with 10$^6$ B16F10 murine melanoma cells. Beginning at day 6 post-implantation, tumor size was measured daily by calipers under light Methfurane anesthesia. The mass of the resulting tumor (in mg) was estimated via the formula (W$^2$×L)/2 where W is the length of the shorter tumor dimension, and L is the length of the longer dimension (in mm). Treatment commenced in each animal when the tumor was 50 mg or larger in size. Each study animal was followed individually, such that Day 1 of treatment for each animal corresponded to the day on which the size of the tumor indicated commencement of dosing. All test compounds were dosed IV via the tail vein, and administered in a volume of 0.2–0.3 mL per 20 g body weight. Animals were observed and weighed daily prior to dosing for establishment of dosing volumes, and daily thereafter until the termination of the study. Results are shown in FIG. 12.

EXAMPLE 24

Tumor Growth Inhibition in a s.c. B16 Melanoma Model: O,O—Pt Chelate

Tumor growth inhibition of poly(HPMA)-GFLG-Ama=Pt(NH$_3$)$_2$, O,O—Pt chelate, 25 kDa (O,O—Pt) versus cisplatin and saline control was evaluated in female C57BL/6 mice. The O,O—Pt chelate and cisplatin were dosed at 17.5 mg Pt/kg and 3 mg/kg, respectively, on a qd×5 schedule. This O,O-chelate dose is near its MTD as is the cisplatin dose. The study was performed as described in Example 23. Results are shown in FIG. 13.

EXAMPLE 25

Tumor Growth Inhibition in a s.c B16 Melanoma Model: N,O—Pt Chelate

Tumor growth inhibition of poly(HPMA)-GFLG-Ama=Pt(NH$_3$)$_2$, N,O—Pt chelate, 25 kDa (N,O—Pt) versus carboplatin and saline control was evaluated in female C57BL/6 mice. The N,O—Pt chelate and carboplatin were dosed at 200 mg Pt/kg and 65 mg/kg, respectively, on a qd×5 schedule. This N,O-chelate dose is near its MTD as is the carboplatin dose. The study was otherwise performed as described in Example 23. Results are shown in FIG. 14.

EXAMPLE 26

Tumor Growth Inhibition in a s.c. Squamous Cell Xenograft Model: N,O—Pt Chelate

Tumor growth inhibition of poly(HPMA)-GFLG-Ama=Pt(NH$_3$)$_2$, N,O—Pt chelate, 25 kDa (N,O—Pt) versus carboplatin and vehicle control (isotonic glucose) was evaluated in groups of 7 BALB/c nu/nu mice per treatment group. Human squamous tumor cells (UMSCC10b) were implanted (10$^6$ cells per site) at four sites (left and right shoulder and left and right flank). The N,O—Pt chelate and carboplatin were dosed at 400 mg Pt/kg and 65 mg/kg, respectively, as a single IP injection. This N,O-chelate dose is near its MTD as is the carboplatin dose. When the tumors reached a group mean of 50 mg, all of the mice were administered the test regimen. Results are shown in FIG. 15.

Changes may be made in the construction and the operation of various components, elements and assemblies described herein or in the steps or the sequence of steps of the methods described herein without departing from the spirit and scope of the invention as defined in the following claims.

The following citations are incorporated be reference herein for details supplementing this application:

REFERENCES

1. Appleton, T. G., Hall, J. R., Neale, D. W., and Thompson, C. S. M., "Reactions of the cis-Diamminediaquaplatinum(II) Cation with 2-Aminomalonic Acid and Its Homologues, Aspartic and Glutamic Acids. Rearrangements of Metastable Complexes with Carboxylate-Bound Ligands to N,O-Chelates and Formation of Di- and Trinuclear Complexes[1]", *Inorg Chem*, 29,3985–3990 (1990n385).

2. Bogdanov, Jr., A. A., et al., *Bioconjugate Chem.* 7:144–149 (1996).

3. Duncan, et al., U.S. Pat. No. 5,965,118 issued Oct. 12, 1999 and assigned to Access Pharmaceuticals, Inc., Dallas, Tex.

4. Duncan, R., et al., *Brit. J Cancer* 55:165–174 (1987).

5. Duncan, R., et al., *Anti-Cancer Drugs* 3:175–210 (1992).

6. Fiebig, H. H., et al., *Proc. Am. Asso. for Cancer Res.* 37:297, Abstract No. 2021 (1996).

7. Filipová-Vopršálová, M., et al., *J. Controlled Release* 17(89–98) (1991).

8. Freise, J., et al., *Arch. Int. Pharmacodyn.* 258:180–192 (1982).

9. Fuji, K., et al., *Proc. Intern. Symp. Control. Rel. Bioact. Mater.* 23:639–640 (1996).

10. Gandolfi, O., "Novel Organoplatinum(II) Complexes and Method for the Preparation Thereof", U.S. Pat. No. 4,614,811.

11. Gandolfi, O., Apfelbaum, H. C., and Blum, J., "Aminomalonato(1,2-diaminocyclohexane)platinum(II): A Competitive Antitumor Compound Within a New Class of Neutral, Chemically Stable, Water Soluble, Functionalized Platinum(II) Complexes", *Inorganic Chimica Acta*, 135, 27–31 (1987).

12. Gianasi, E., Wasil, M., Evagorou, E. G., Keddle, A., Wilson, G., and Duncan, R., "HPMA copolymer platinates as novel antitumour agents: in vitro properties, pharmacokinetics and antitumour activity in vivo", Eur J Cancer, 35, 994–1002 (1999).

13. Gibson, D., Rosenfeld, A., Apfelbaum, H., and Blum, J., "Multinuclear ($^{195}$Pt, $^{15}$N, $^{13}$C) NMR Studies of the Reactions between cis-Diaminediaquaplatinum(II) Complexes and Aminomalonate", *Inorg Chem*, 29, 5125–5129 (1990).

14. Han, M. J., et al., *J. Bioact. and Biocompat. Polymers* 9:142 (1994).

15. Johnsson, A., and Cavallin-Ståhl, E., *Anti-Cancer Drugs* 7:70–77 (1996).

16. Neuse, E. W., et al., *J. Inorganic and Organometallic Polymer* 5(3):195–207 (1995).

17. Prestayko, A. W., *Cancer and Chemo. Vol III* (Crooke, et al., Eds.) Academic Press, NY, 133–154 (1981).

18. Schechter, B., et al., *J. Controlled Release* 10:75–87 (1989).

19. Seymour, L. W., et al., *J. of Biomed. Mat. Res.* 21:1341–1358 (1987).

20. Steerenberg, P. A., et al, *International Journal of Pharmaceutics* 40:51–62 (1987).

21. Sur, B., et al, *Oncology* 40:372–376(1983).

22. Talebian, A., et al. (a), "Synthesis and Characterization of a Series of Water Soluble Amidomalonato-(1R,2R-Cyclohexanediamine)Platinum(II) Complexes", *J. Coor. Chem*, 22,165–173 (1990).

23. Talebian, A., et al. (b), "Murine anti-tumor activity of new water soluble platinum (II) complexes with reduced toxicity", *Anti-Cancer Drug Design*, 5, 371–380 (1990).

24. Weiss, R. B., et al., *Drugs* 46(3):360–377 (1993).

25. Bogdanov et al., "Graft Co-Polymer Adducts of Platinum (II) Compounds", U.S. Pat. No. 5,871,710.

26. Bancroft et al., "$^{195}$Pt NMR Kinetic and Mechanistic Studies of cis- and trans-Diamminedichloroplatinum(II) Binding to DNA", J. Am Chem. Soc. 112: 6860–6871 (1990).

27. Kopecek, et al. "Synthetic Polymeric Prodrugs", U.S. Pat. No. 5,037,883.

28. Matsumura et al. "A new concept for macromolecular therapeutics in cancer therapy: mechanism of tumoritropic accumulation of proteins and the antitumor agent SMANCS", Cancer Res. 46: 6378–6392 (1986).

29. Yoguchi, et al. "Early phase tumor accumulation of macromolecules: a great difference in clearance rate between tumor and normal tissues, Jpn. J. Cncer Res. 89: 307–314 (1998).

30. Song, et al. "Synthesis and hydrolytic properties of polyphosphazene/(diamine) platinum/saccharide conjugates" J. Controlled Release 55: 161–170 (1998).

31. Sohn et al. "Synthesis and antitumor activity of novel polyphosphazene(diamine)platinum(II) conjugates" Inter. J. of Pharmaceutics 153: 79–91 (1997).

32. Li, et al. "Complete Regression of Well-established Tumors Using a Novel Water-soluble Poly(L-Glutamic Acid)-Paclitaxel Conjugate" Cancer Research 58: 2404–2409 (1998).

33. Mendichi, R. et al. "Molecular Characterization of Polymeric Antitumor Drug Carriers by Size Exclusion Chromatography and Universal Calibration" J. Liq. Chrom. and Rel Tech. 19: 1591–1605 (1996).

34. Pinciroli, et al. "$^1$H NMR Characterization of Methacrylamide Polymer Conjugates with the Anti-Cancer Drug Doxorubicin" Magn. Reson. Chem. 35: 2–8 (1997).

35. Gandolfi et al. Inorg. Chim Acta 135: 27–31 (1987).

36. Appleton et al. "Reaction of cis-Diamminediaquaplatinum(II) cation with N-Acetylglycine" Inorg. Chem. 28: 815–819 (1989).

37. Danishefsky et al. "Conversion of Carboxyl Groups of Mucopolysaccharides into Amides of Amino Acid Esters" Carbohyd. Res. 16: 199–205 (1971).

38. Tsujihara et al, "Novel Organic Platinum Complex and Process for the Preparation Thereof" U.S. Pat. No. 4,882,447.

39. Chao, et al. "Interaction of Cis Platinum(II) Compounds with Poly(1-glutamate). A Doubly Anchored Spin-Label and a Doubly Anchored Chromophore-Label' J. Am. Chem. Soc. 99: 8024–8032 (1977).

40. Criado, et al. "Structural Characterization, Kinetic Studies, and in Vitro Biological Activity of New cis-Diamminebis-cholylglycinate(O,O') Pt(II) and cis Diannminebisursodeoxycholate(O,O') Pt(II) Complexes" Bioconj. Chem. 11: 167–174 (2000).

41. Rosenberg et al. "Platinum Compounds: A New Class of Potent Antitumour Agents" Nature (London) 222: 385 (1969).

42. Sur et al. "Effect of liposomal Encapsulation of Cis-platinum diamminodichloride in the Treatment of Ehrlich Ascites Carcinoma" Oncology 40: 372–6 (1983).

43. Talebian, et al. "Aspartato(1,2-cyclohexanediamine) platinum(II) complexes: synthesis and characterization; effects of minor impurities on antitumor activity" Inorg. Chim. Acta 179: 281–287 (1991).

44. Gibson, D., Rosenfeld, "Multinuclear ($^{195}$Pt, $^{15}$N, $^{13}$C) NMR Studies of the Reactions between cis-Diaminediaquaplatinum(II) Complexes and Aminomalonate", *Inorg Chem*, 29: 5125–5129 (1990).

45. Harrap, "Preclinical Studies Identifying Carboplatin as a Viable Cisplatin Alternative" Cancer Treat. Rev. 21(Suppl. A): 21–33 (1985).

46. Posner et al, "The Role of Induction Chemotherapy in the Curative Treatment of Squamous Cell Cancer of the Head and Neck" Semin Oncol, 27(4 Suppl 8):13–24 (2000).

47. Steerenberg et al, "Liposomes as Drug Carrier System for Cis-diamminedichloroplatinum(II). II. Antitumor Activity in vivo, Induction of Drug Resistance, Nephrotoxicity and Pt Distribution" Cancer Chemother Pharmacol.21:299–307 (1988).

48. K. D. Paull et al, "Display and Analysis of Patterns of Differential Activity of Drugs against Human Tumor Cell Lines: Development of Mean Graph and COMPARE Algorithm" J.Natl.Cancer Inst. 81: 1088 (1989).

49. Physician's Desk Reference 51th ed, Medical Economics:Montvale, N.J., 1997 Devita et al. CANCER Principles & Practice of Onology 4$^{th}$ ed, J. B. Lippincott Company: Philadelphia, Pa. 1993, p395.

50. Seymour, "Passive Tumor Targeting of Soluble Macromolecules and Drug Conjugates" Crit Rev Ther Drug Carrier Syst 9(2):135–87 (1992).

51. Veronese et al. "Bioconjugation in Pharmaceutical Chemistry" Farmaco 54(8):497–516 (1999).

52. Seymour et al. "Influence of Molecular Weight on Passive Tumour Accumulation of a Soluble Macromolecular Drug Carrier" 31A: 766–770 (1995).

53. Seymour et al, "The Pharmacokinetics of Polymer-bound Adriamycin" Biochem Pharmacol. 39: 1125–31 (1990).

54. Pimm et al, "Gamma Scintigraphy of the Biodistribution of 123I-labelled N-(2-hydroxypropyl) methacrylamide Copolymer-doxorubicin Conjugates in Mice with Transplanted Melanoma and Mammary Carcinoma" J Drug Target.3: 375–83 (1996).

55. Duncan et al, "Preclinical Toxicology of a Novel Polymeric Antitumour Agent: HPMA Copolymer-doxorubicin (PK1)" Hum Exp Toxicol. 17: 93–104 (1998).

56. Thomson et al, "Population pharmacokinetics in phase I drug development: a phase I study of PK1 in patients with solid tumours" Br J Cancer. 81: 99–107 (1999).

57. Minko et al, "Efficacy of the Chemotherapeutic Action of HPMA Copolymer-bound Doxorubicin in a Solid Tumor Model of Ovarian Carcinoma" Int J Cancer. 86: 108–17 (2000).

58. Fraier et al, "Determination of a new polymer-bound paclitaxel derivative (PNU 166945), free paclitaxel and 7-epipaclitaxel in dog plasma and urine by reversed-phase high-performance liquid chromatography with UV detection" J Chromatogr A 797: 295–303 (1998).

59. Caiolfa et al, "Polymer-bound Camptothecin: Initial Biodistribution and Antitumor Activity Studies" J Control Release. 65: 105–19 (2000).

60. Li et al, "Biodistribution of paclitaxel and poly(L-glutamic acid)-paclitaxel conjugate in mice with ovarian OCa-1 tumor" Cancer Chemother Pharmacol., 46: 416–22 (2000).

61. Conover et al, "Camptothecin Delivery Systems: enhanced efficacy and tumor accumulation of camptothecin following its conjugation to polyethylene glycol via a glycine linker" Cancer Chemother Pharmacol, 42: 407–14 (1998).

62. Duncan, "Drug-polymer conjugates: Potential for improved chemotherapy" Anti-Cancer Drugs, 3: 175–210 (1992).

63. Gianasi, et al. "HPMA Copolymer Platinates as Novel Antitumour Agents: In Vitro Properties, Pharmacokinetics and Antitumour Activity In Vivo" European J. Cancer 35: 994–1002 (1999).

64. Schechter et al, "Increased therapeutic efficacy of cis-platinum complexes of poly-L-glutamic acid against a murine carcinoma" Int J Cancer 1987 Mar 15;39(3):409–13.

65. Bogdanov, Jr. et al., "An adduct of cis-diamminedichloroplatinum(II) and poly(ethylene glycol) poly(L-lysine)-succinate: synthesis and cytotoxic properties" Bioconjug Chem. 1996 January-February;7(1): 144–9.

66. Han, et al., "Synthesis and Antitumor Activity of Polyanion-Pt-complexes containing Alicyclic Amines as Ligands" J. Bioactive and Compatible Polymers 9: 142–151 (1994).

67. Johnsson et al. "A topographic study on the distribution of cisplatin in xenografted tumors on nude mice" Anti-Cancer Drugs 7: 70–77 (1996).

68. Fiebig, et al., "GB-21, a novel platinum polymer with antitumor activity in human renal and mammary xenografts" Proc. American Association for Cancer Research, 37:297 abs# 2021 (1996).

69. Filipova-Voprsalova et. al., "Biodistribution of trans-1,2-diaminocyclohexane-trimellitoplatinum(II) attached to macromolecular carriers" J. Controlled Release 17:89–98 (1991).

70. Fuji et al, "Control of Pharmacokinetics and Nephrotoxicity of cis-DDP by Alginate" Proc. Int. Symp. Controlled Rel. Bioact. Matr., 23: 639–40 (1996).

71. Neuse, et al. "cis-Diaminedichloroplatinum(II) complexes reversibly bound to water-soluble polyasparatamide carrier for chemotherapeutic applications. I. Platinum coordination to carrier-attached ethylenediamine ligands" J. Inorg. Organomet Polym., 1(2): 147–165 (1995).

72. Schechter, et al., "Soluble polymers as carriers of cis-platinum" J. Controlled Release 10: 75–87 (1989).

73. Heppeler et al, "Receptor targeting for tumor localisation and therapy with radiopeptides" Curr Med Chem 2000 Sep;7(9):971–94.

74. Schlaeppi et al. "Targeting vascular endothelial growth factor (VEGF) for anti-tumor therapy, by anti-VEGF neutralizing monoclonal antibodies or by VEGF receptor tyrosine-kinase inhibitors" Cancer Metastasis Rev. 18: 473–81 (1999).

75. Sudimack et al. "Targeted drug delivery via the folate receptor" Adv Drug Deliv Rev. 41: 147–62 (2000).

76. Dubowchik et al. "Receptor-mediated and enzyme-dependent targeting of cytotoxic anticancer drugs" Pharmacol Ther 83:67–123 (1999).

77. Weiner, "An overview of monoclonal antibody therapy of cancer" Semin Oncol 26, Suppl 12: 41–50 (1999).

78. Buolamwini, "Novel anticancer drug discovery" Curr Opin Chem Biol 3:500–9 (1999).

79. McIntosh et al, "Pharmacokinetics and tissue distribution of cisplatin and conjugates of cisplatin with carboxymethyldextran and A5B7 monoclonal antibody in CD1 mice" J Pharm Sci. 86: 1478–83 (1997).

80. Hata et al, "Immunotargeting chemotherapy for AFP-producing pediatric liver cancer using the conjugates of anti-AFP antibody and anti-tumor agents" J Pediatr Surg. 27: 724–7 (1992).

81. Gust et al, "Investigation of the configurational and conformational influences on the hormonal activity of 1,2-bis(2,6-dichloro-4-hydroxyphenyl)ethylenediamines and of their platinum(II) complexes. 1. Synthesis, estradiol receptor affinity, and estrogenic activity of diastereomeric [N-alkyl- and N,N'-dialkyl-1,2- bis(2,6-dichloro-4-hydroxyphenyl) ethylenediamine]dichloroplatinum(II) complexes" J Med Chem. 38: 2070–9 (1995).

82. DiZio et al, "Estrogen platinum-diamine complexes: preparation of a non-steroidal estrogen platinum-diamine complex labeled with platinum-191 and a study of its binding to the estrogen receptor in vitro and its tissue distribution in vivo" J Steroid Biochem Mol Biol 42: 363–73 (1992).

83. Vitols et al, "Platinum-folate compounds: synthesis, properties and biological activity" Adv Enzyme Regul. 26: 17–27 (1987).

84. Julyan et al, "Preliminary clinical study of the distribution of HPMA copolymers bearing doxorubicin and galactosamine" J Control Release 57: 281–90 (1999).

85. Appleton et al. "Reactions of the cis-Diamminediaquaplatinum(II) Cation with 2-Aminomalonic Acid and Its Homologues, Aspartic and Glutamic Acids. Rearrangements of Metastable Complexes with Carboxylate-Bound Ligands to N,O-Chelates and Formation of Di- and Trinuclear Complexes", Inorg Chem, 29: 3985–3990 (1990).

86. Talebian, et al. "Synthesis and Characterization of a Series of Water Soluble Amidomalonato-(1R,2R-Cyclohexanediamine)Platinum(II) Complexes", *J Coor. Chem*, 22,165–173 (1990).

87. Appleton et al. "The Chemistry of Cisplatin in Aqueous Solution" in Platinum-Based Drugs in Cancer Therapy, Kelland and Farrell eds, Humana Press Totowa, N.J., 2000.

88. Sohn, et al. "Synthesis and antitumor activity of novel polyphosphazene(diamine)platinum(II) conjugates" Inter. J. Pharmaceutics 153: 79–91 (1997).

What is claimed:

1. A composition for use in tumor treatment, comprising:
a polymer-platinum complex designed to accumulate at a tumor site and composed of an N-alkyl acrylamide copolymer of the form:

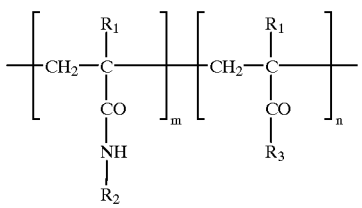

where m=0 and n=100 or where the ratio of m:n is 0.1–99.9, where $R_1$ is H or $CH_3$, $R_2$ is a lower alkyl or lower hydroxyalkyl group, and $R_3$ is an oligopeptide side chain spaced along the polymer for complexing with a platinum compound, said side chains (i) composed of an oligopeptide attached at one end to the polymer and at the other end, at least primarily via a N,O-amidomalonate complex, to the platinum compound and (ii) comprising at least one linkage designed to be cleaved under selected physiological conditions to yield a platinum compound which has, or is converted in vivo to have, anti-tumor activity.

2. A composition for use in tumor treatment, comprising:
a polymer-platinum complex designed to accumulate at a tumor site and composed of an N-alkyl acrylamide copolymer of the form:

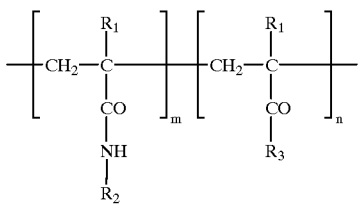

where m=0 and n=100 or where the ratio of m:n is 0.1–99.9, where $R_1$ is H or $CH_3$, $R_2$ is a lower alkyl or lower hydroxyalkyl group, and $R_3$ is an oligopeptide side chain wherein said oligopeptide is Gly-$(W)_p$-Gly where p is 0–3 and W is an amino acid or combination of any amino acids having side chains spaced along the polymer for complexing with a platinum compound, said side chains (i) composed of an oligopeptide attached at one end to the polymer and at the other end, at least primarily via a N,O-amidomalonate complex, to the platinum compound and (ii) comprising at least one linkage designed to be cleaved under selected physiological conditions to yield a platinum compound which has, or is converted in vivo to have, anti-tumor activity.

3. A composition for use in tumor treatment, comprising:
a polymer-platinum complex designed to accumulate at a tumor site and composed of an N-alkyl acrylamide copolymer of the form:

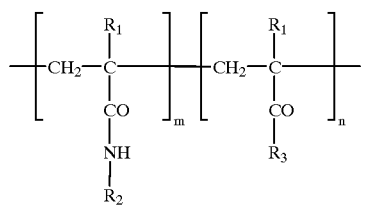

where m=0 and n=100 or where the ratio of m:n is 0.1–99.9, where $R_1$ is $CH_3$, $R_2$ is 2-hydroxypropyl, and $R_3$ is Gly-Phe-Leu-Gly-Ama or Gly-Gly-Ama having side chains spaced along the polymer for complexing with a platinum compound, said side chains (i) composed of an oligopeptide attached at one end to the polymer and at the other end, at least primarily via a N,O-amidomalonate complex, to the platinum compound and (ii) comprising at least one linkage designed to be cleaved under selected physiological conditions to yield a platinum compound which has, or is converted in vivo to have, anti-tumor activity.

4. A method of treating solid tumor in a subject with a platinum compound, the method comprising preparing a polymer-platinum complex composed of an N-alkyl acrylamide polymer having side chains spaced along the polymer for complexing with a platinum compound, said side chains (i) composed of an Gly-$(W)_p$-Gly where p is 0–3 and W is an amino acid or combination of any amino acids attached at one end to the polymer and at the other end to the platinum compound via a N, O-amidomalonate complex and (ii) comprising at least one linkage designed to be cleaved under selected physiological conditions to yield the platinum compound which has, or is converted in vivo to have, anti-tumor activity; and parenterally administering a pharmaceutically effective amount of the complex to the subject.

5. A method of treating a solid tumor in a subject with a platinum compound, the method comprising preparing a polymer-platinum complex composed of an N-alkyl acrylamide polymer having side chains spaced along the polymer for complexing with a platinum compound, said side chains (i) composed of Gly-Phe-Leu-Gly or Gly-Gly oligopeptide attached at one end to the polymer and at the other end to the platinum compound via a N, O-amidomalonate complex and (ii) comprising at least one linkage designed to be cleaved under selected physiological conditions to yield the platinum compound which has, or is converted in vivo to have, anti-tumor activity; and parenterally administering a pharmaceutically effective amount of the complex to the subject.

6. A method of treating a solid tumor in a subject with a platinum compound, the method comprising preparing a polymer-platinum complex compound of an N-alkyl acrylamide polymer having side chains spaced along the polymer for complexing with a platinum compound, said side chains (i) composed of an oligopeptide attached at one end to the polymer and at the other end to the platinum compound via a N, O-amidomalonate complex and (ii) comprising at least one linkage designed to be cleaved under selected physiological conditions to yield the platinum compound which has, or is converted in vivo to have, anti-tumor activity; and parenterally administering a pharmaceutically effective amount of the complex to the subject, wherein said oligopeptide is Gly-$(W)_p$-Gly where p is 0–3 and W is an amino acid or combination of any amino acids.

7. A method of treating a solid tumor in a subject with a platinum compound, the method comprising preparing a polymer-platinum complex compound of an N-alkyl acrylamide polymer having side chains spaced along the polymer for complexing with a platinum compound, said side chains (i) composed of an oligopeptide attached at one end to the polymer and at the other end to the platinum compound via a N, O-amidomalonate complex and (ii) comprising at least one linkage designed to be cleaved under selected physiological conditions to yield the platinum compound which has, or is converted in vivo to have, anti-tumor activity; and parenterally administering a pharmaceutically effective amount of the complex to the subject, wherein said oligopeptide is Gly-Phe-Leu-Gly or Gly-Gly.

* * * * *